US009416425B2

(12) United States Patent
Fach et al.

(10) Patent No.: US 9,416,425 B2
(45) Date of Patent: Aug. 16, 2016

(54) ASSAY FOR DETERMINING A MOLECULAR RISK ASSESSMENT OF A COMPLEX POLYMICROBIAL SAMPLE SUSPECTED TO CONTAIN AN EHEC

(75) Inventors: Patrick Fach, Creteil (FR); Marie Bugarel, Pont du Casse (FR); Lothar Beutin, Berlin (DE)

(73) Assignee: Agence Nationale de Securite Sanitaire de l'Alimentation, de l'Environment et du Travail, Maisons-Alfort (FR)

( * ) Notice: Subject to any disclaimer, the term of this patent is extended or adjusted under 35 U.S.C. 154(b) by 786 days.

(21) Appl. No.: 13/389,957

(22) PCT Filed: Aug. 11, 2010

(86) PCT No.: PCT/IB2010/053631
§ 371 (c)(1),
(2), (4) Date: Apr. 27, 2012

(87) PCT Pub. No.: WO2011/018762
PCT Pub. Date: Feb. 17, 2011

(65) Prior Publication Data
US 2012/0202204 A1    Aug. 9, 2012

(30) Foreign Application Priority Data
Aug. 11, 2009   (EP) ................................ 09290621

(51) Int. Cl.
*C12Q 1/68* (2006.01)
(52) U.S. Cl.
CPC ..................................... *C12Q 1/689* (2013.01)
(58) Field of Classification Search
None
See application file for complete search history.

(56) References Cited

U.S. PATENT DOCUMENTS

| | | | |
|---|---|---|---|
| 6,291,168 B1 * | 9/2001 | Musso ........................ | 435/6.16 |
| 8,507,249 B2 * | 8/2013 | Finlay et al. ............... | 435/252.3 |
| 2006/0051769 A1 | 3/2006 | Barts | |
| 2006/0094034 A1 * | 5/2006 | Brousseau et al. ................ | 435/6 |
| 2007/0041997 A1 | 2/2007 | Finlay et al. | |

OTHER PUBLICATIONS

Vlisidou et al. (2006) FEMS Microbiol Lett 263 : pp. 32-40.*
Blanco et al. (2004) J. Clin. Microbiol. Vo. 42 No. 2 pp. 645-651.*
Paton et al. (1998) J. Clin. Microbiol. vol. 36 No. 2 pp. 598-602.*
Beutin et al. (on line publication Jan. 16, 2009) J of Applied Microbiology 106 (2009): 1122-1132.*
Z1829 sequence disclosed by Vlisidou alignment and history 2009.*
CP001368 sequence comprising Z1829 sequence submitted Jan. 2009.*
Gilmour et al., "Isolation and Genetic Characterization of a Coinfection of Non-O157 Shiga Toxin-Producing *Escherichia coli*," Journal of Clinical Microbiology, 45: 3771-3773 (2007).
Garrido P. et al. STEC-EPEC Oligonucleotide Microarray: A New Tool for Typing Genetic Variants of the LEE Pathogenicity Island of Human and Animal Shiga Toxin—Producing *Escherichia coli* (STEC) and Enteropathogenic *E. coli* (EPEC) Strains, Clinical Chemistry, 52:2 (2006).
Coombes, Molecular Analysis as an Aid to Assess the Public Health Risk of Non-O157 Shiga Toxin-Producing *Escherichia coli* Strains, Applied and Environmental Microbiology, 74, pp. 2153-2160, 2008.
Beutin, Evaluation of the "GeneDisc" Real-Time PCR System for Detection of Enterohaemorrhagic *Escherichia coli* (EHEC) O26, O103, O111, O145 and O157 Strains According to Their Virulence Markers and Their O- and H-Antigen-Associated Genes, Journal of Applied Microbiology, 106, pp. 1122-1132, 2009.
Creuzburg, Molecular Characterization and Distribution of Genes Encoding Members of the Type III Effector NleA Family Among Pathogenic *Escherichia coli* Strains, Journal of Clinical Microbiology, 45, pp. 2498-2507, 2007.
Konczy, Genomic O Island 122, Locus for Enterocyte Effacement, and the Evolution of Virulent Verocytotoxin-Producing *Escherichia coli*, Journal of Bacteriology, 190, pp. 5232-5240, 2008.
Perelle, Detection by 5'-nuclease PCR of Shiga-Toxin Producing *Escherichia coli* O26, O55, O91, O103, O111, O113, O145 and O157:H7, Associated with the World's Most Frequent Clinical Cases. Molecular and Cellular Probes, 18, pp. 185-192, 2004.
Vlisidou, Identification and characterization of EspK. a Type III Secreted Effector Protein of Enterohaemorrhagic *Escherichia coli* O157:H7, FEMS Microbiol. Lett, 263, 32-40, 2006.
Ogura, Extensive Genomic Diversity and Selective Conservation of Virulence-Determinants in Enterohemorrhagic *Escherichia coli* Strains of O157 Serotypes. Genome Biology, 8, R138, 2007.
Bugarel, Micro-Array for the Identification of Shiga Toxin-Producing *Escherichia coli* (STEC) Seropathotypes Associated with Hemorrhagic Colitis and Hemolytic Uremic Syndrome in Humans International Journal of Food Microbiology, 142, 318-329, 2010.

* cited by examiner

*Primary Examiner* — Suchira Pande
(74) *Attorney, Agent, or Firm* — Morgan, Lewis & Bockius LLP

(57) ABSTRACT

The present invention relates to a process to perform a molecular risk assessment (MRA) upon a sample suspected to contain an enterohemorrhagic *Escherichia coli* (EHEC), comprising the steps: contacting said sample or DNA isolated therefrom with a pair of primers derived from the following target genes stx1, stx2, eae and/or espk; wherein the process is characterized in that if amplification products are detected for each of the target genes in the first step, in a second step said sample or DNA isolated therefrom is contacted with a pair of primers derived from the following target genes nleB, nleH1-2, nleE, ent/espL2, eae subtypes γ, β, ε and θ and the target genes rfbE (O157), wbdl (O111), wzx (O26); ihp1 (O145), wzx (O103); and detecting the presence or the absence of an amplification product for each of the target genes.

23 Claims, No Drawings

ASSAY FOR DETERMINING A MOLECULAR RISK ASSESSMENT OF A COMPLEX POLYMICROBIAL SAMPLE SUSPECTED TO CONTAIN AN EHEC

RELATED APPLICATIONS

The present application is a U.S. National Phase Application of International Application No. PCT/IB2010/053631 (filed Aug. 11, 2010) which claims priority to European Application No. 09290621.3 (filed Aug. 11, 2009) which are hereby incorporated by reference in their entirety.

SEQUENCE LISTING SUBMISSION VIA EFS-WEB

A computer readable text file, entitled "045636-5183_SequenceListing.txt," created on or about Feb. 10, 2012, with a file size of about 15 kb contains the sequence listing for this application and is hereby incorporated by reference in its entirety.

Since the early 1980s, Shiga toxin-producing *Escherichia coli* (STEC) have emerged as a major cause of food-borne infections (Karmali et al. 1983, Riley et al. 1983). STEC can cause diarrhea in humans and some STEC strains may cause life-threatening diseases such as Hemorrhagic Colitis (HC) and Haemolytic Uraemic Syndrome (HUS). According to their human pathogenicity the latter strains were also designated as enterohaemorrhagic *E. coli* (EHEC) (Levine 1987, Nataro and Kaper 1998). Numerous cases of HC and HUS have been attributed to EHEC serotype O157:H7 strains, but it has now been recognized that other serotypes of STEC belong to the EHEC group. A STEC seropathotype classification (from A to E) based upon the serotype association with human epidemics, HUS and diarrhea has been developed as an aid to assess the clinical and public health risks associated with non-O157 EHEC and STEC strains (Karmali et al. 2003). Recent data from Enter-Net, a global surveillance consortium of 35 countries that tracks enteric infectious diseases, showed that the number of human diseases caused by non-O157 STEC and EHEC increased globally by 60.5% between 2000 and 2005, while at the same time the number of cases linked to EHEC O157 increased by only 13% (Anonymous 2005). Among the top five of non-O157 EHEC serotypes most frequently implicated in hemorrhagic diseases in 2005, 80% belong to seropathotype B and 20% belong to seropathotype C (Anonymous 2005). None belong to the less-virulent STEC seropathotypes D and E, suggesting that selection for highly virulent strains is currently taking place.

The production of Shiga toxin by EHEC is the primary virulence trait responsible for HUS, but many *E. coli* non-O157:H7 strains that produce Shiga toxin do not cause HUS. Identification of human virulent STEC by unique detection of stx genes may be misleading since not all STEC strains are clinically significant to humans (EFSA 2007). In addition, to produce one or both types of Shiga toxins, typical EHEC strains harbour a genomic island, called the "locus of enterocyte effacement" (LEE). This locus was first identified in enteropathogenic *E. coli* (EPEC), predominant cause of infant diarrhea in developing countries. The LEE carries genes encoding functions for bacterial colonization of the gut and for destruction of the intestinal mucosa thus contributing to the disease process (Nataro and Kaper 1998). The LEE encoded eae-gene product intimin is directly involved in attaching and effacing (A/E) process and serves as an indicator for the A/E function in the bacteria (Zhang et al. 2002). Considerable heterogeneity has been identified among the DNA sequences of the eae genes, especially in their 3'-end region, which has led to the classification of at least 21 intimin subtypes. Among these, the eae-γ subtype has commonly been found in EHEC O157:H7 and O145:H28, whereas eae-β, eae-ε and eae-θ subtypes have commonly been detected in EHEC O26:H11, O103:H2, and O111:H8 respectively (Oswald et al. 2000; Tarr and Whittam 2002).

The LEE includes regulatory elements, a type III secretion system (TTSS), secreted effector proteins, and their cognate chaperon (Elliott et al. 1998, Perna et al. 1998). In addition to the intimin, most of the typical EHEC strains harbour the plasmid encoded enterohaemolysin (ehxA) which is considered as an associated virulence factor (Nataro and Kaper 1998). However, the LEE and the enterohaemolysin are not found in all STEC causing HC and HUS and the corresponding strains were designated as atypical EHEC (Nataro and Kaper 1998). Atypical EHEC are less frequently involved in hemorrhagic diseases than typical EHEC, but are a frequent cause of diarrhea, indicating additional virulence determinants play a role in the pathogenicity (Brooks et al. 2005, Eklund et al. 2001).

Virulence in bacterial pathogens is modulated by the acquisition of mobile genetic elements such as genomic islands (Lawrence 2005). One class of genomic islands, called pathogenicity islands (PAIS) constitute a flexible gene pool contributing to pathogen evolution and virulence potential and can be used as a genetic signature of new and emerging pathogens. A huge number of type III effectors which are encoded by PAIS outside the LEE have been described in EHEC and in enteropathogenic *E. coli* (EPEC) strains.

Techniques exist to determine the presence of a STEC contamination in a sample by for instance detecting the presence of the stx1/stx2 genes and the eae gene (Loukiadis et al. 2006). But as explained above the genetic basis of STEC pathogenicity is a lot more complex than the presence or absence of one or both of these genes. In a complex sample, which may comprise a mixture of strains, the presence of the stx1/2 genes and the LEE is also not always indicative of the presence of an EHEC in this sample.

Therefore no reliable tests exist at the present time to screen a complex poly-microbial sample (e.g. food, fecal, environmental samples) for the presence of EHEC. Given that some EHEC strains can cause very serious health problems in humans, workers using existing methods must discard a sample whenever a STEC strain is detected therein; even though it is likely this STEC does not pose a threat to human health. Existing methods therefore result in a large amount of wastage due to lack of discrimination between non-pathogenic STEC strains and EHEC strains.

In addition due to the nature of the samples being tested, these can comprise a number of diverse bacterial strains each comprising a different complement of genes and hence each presenting a different possible level of pathogenicity.

Therefore a more complex and nuanced assay is required to allow a more complete molecular risk assessment to be performed upon a sample suspected of comprising a STEC, this new assay should be able to determine the risk posed/pathogenicity of a particular contaminating STEC strain. This assay should also because of its increased complexity allow the identification of known virulent EHEC strains which cannot at the present time be routinely identified in a sample.

In accordance with a first aspect of the present invention, there is provided a process to perform a molecular risk assessment (MRA) upon a sample suspected to contain a Shiga toxin-encoding *Escherichia coli* (STEC), comprising the steps:

contacting said sample or DNA isolated therefrom with a pair of primers derived from the following target genes:
stx1;
stx2; and at least one of the following target genes:
eae;
espK;
wherein said process is characterised in that it also comprises contacting said sample or DNA isolated therefrom with a pair of primers derived from the following target genes:
nleB;
nleH1-2;
nleE;
ent/espL2;
and detecting the presence or the absence of an amplification product for each of said target genes.

This process allows a detailed molecular risk assessment to be made upon a sample suspected of containing a STEC contaminant and in this risk assessment a worker can identify which of the panel of selected target genes the contaminant comprises and from this determine whether this contaminant pose a threat to human health or not. In particular this process may be used to determine whether or not a STEC strain is an EHEC strain. The inventors have shown that the presence of all these target genes in a strain correlates with the strain being an EHEC strain.

The stx1 and stx2 genes encode the shiga toxins and their presence is therefore essential for pathogenicity. The eae gene (intimin) is encoded by the LEE genomic island and is therefore a useful marker for this genomic island which is known to be associated with typical EHEC strains and with EPEC strains. The inventors have also established that some nle genes or alleles of these genes and the espK gene (Z1829) are linked to EHEC strains and can therefore be used in place of or in addition to eae.

Some EHEC and EPEC strains also share other genomic islands in addition to the LEE which encode various effector proteins. These non-LEE encoded effector proteins are encoded by large panel of nle genes which are more or less associated with the virulence of *E. coli*.

Consequently, the presence just one of the genes stx1, stx2, eae, espK and a selected nle gene such as nleB, does not provide sufficient information to definitively predict the presence of an EHEC in a complex poly-microbial sample (e.g. food or fecal samples). As a number of foods which are not contaminated by EHEC comprise bacteria with at least one of these genes, they can't be use by themselves as a marker of EHEC. However, when the minimum complement according to this first aspect of the present invention is present in the same sample this can be used as a reliable predictor of virulence as demonstrated below.

Given the fact that it is not realistic to get a unique marker of EHEC strains as has been achieved for other pathogenic bacteria such as *Salmonella* spp., the inventors have developed and refined a process based on the detection of selected targets to screen poly-microbial samples (e.g. food, fecal, environmental samples). This process is based on a multiparametric approach based on the detection of stx1/2 and eae (and/or espK) together with at least the following genes: ent/espL2, nleB, nleE and nleH1-2.

The nle genes can be derived from different mobile genetic elements, including genomic islands. The inventors focused their efforts on the detection of the genes of two genomic islands: the OI#122 genes ent/espL2 (Z4326), nleB (Z4328), nleE (Z4329) and the OI#71 genes: nleF (Z6020), nleH1-2 (Z6021), nleA (Z6024). They found that the OI#122 genes ent/espL2 (Z4326), nleB (Z4328), nleE (Z4329) and the OI#71 gene nleH1-2 (Z6021) (names in brackets are unique Genbank identifiers), were closely associated with typical EHEC strains and with some EPEC strains.

This process therefore allows a worker to routinely determine firstly whether or not a sample comprises a STEC contaminant and secondly allows a worker to determine whether or not this STEC strain is likely to be an EHEC strain.

All the steps of this process can be performed at the same time using for instance a series of amplification reactions or a multiplex amplification reaction. By way of example, a multiplex amplification reaction based on the GeneDisc® system has been used by the inventors. The GeneDisc® system is a recent innovation in the field of DNA amplification using GeneSystems® PCR technology (Beutin et al. 2009) which allows the simultaneous detection of multiple targets in reaction microchambers preloaded with the reagents necessary for detecting and quantifying the required targets (Beutin et al. 2009, Yaradou et al. 2007).

Alternatively the steps can be performed at different times. For instance a sample can be initially analysed for the presence of the stx1, stx2 and eae and/or espK genes. If the results of this reaction are positive the sample can then be analysed for the presence of the remaining virulence determinants nleB, nleH1-2, nleE and ent/espL2 and a MRA made using both sets of results.

In the present invention any set of suitable primers may be used to amplify a target gene so as to produce a detectable amplification product. Most normally this will be a pair of primers separated by a number of base pair from each other in the target gene. However a single primer may be used if this leads to a detectable amplification product or alternatively more than two primers may be used to amplify one or more of the target genes. All such variations are encompassed by the present invention.

In particular the present invention provides a process to perform a MRA upon a sample suspected to contain a EHEC, comprising the steps:
contacting said sample or DNA isolated therefrom with a pair of primers derived from the following target genes:
stx1, using at least one primer defined by SEQ ID NO: 1 or SEQ ID NO: 2, or a fragment of at least fifteen nucleotides thereof;
stx2 using at least one primer defined by SEQ ID NO: 1 or SEQ ID NO: 2, or a fragment of at least fifteen nucleotides thereof; and at least one of the following target genes:
eae using at least one primer defined by SEQ ID NO: 7 or SEQ ID NO: 8, or a fragment of at least fifteen nucleotides thereof;
espK using at least one primer defined by SEQ ID NO: 82 or SEQ ID NO: 83, or a fragment of at least fifteen nucleotides thereof;
wherein said process is characterised in that it also comprises contacting said sample or DNA isolated therefrom with a pair of primers derived from the following target genes:
nleB using at least one primer defined by SEQ ID NO: 16, SEQ ID NO: 17, SEQ ID NO: 79 or SEQ ID NO: 80 or a fragment of at least fifteen nucleotides thereof;
nleH1-2 using at least one primer defined by SEQ ID NO: 25 or SEQ ID NO: 26, or a fragment of at least fifteen nucleotides thereof;
nleE using at least one primer defined by SEQ ID NO: 19 or SEQ ID NO: 20, or a fragment of at least fifteen nucleotides thereof;
ent/espL2 using at least one primer defined by SEQ ID NO: 13 or SEQ ID NO: 14, or a fragment of at least fifteen nucleotides thereof;

and detecting the presence or the absence of an amplification product for each of said target genes.

The inventors have found that this process can be used to identify a wide range of O157 EHEC strains as well as other pathogenic EHEC strains of different serotypes for instance O103, O111, O26, O145, O5, O55, O45, O118, O121, O123, O165, O172, O15. All eae-negative STEC stains were also negative for the set of nle genes investigated in this study. In contrast, nle genes were present in typical EHEC, including the new emerging serotypes. Atypical EHEC i.e. O91:H21 and O113:H21 known to rarely cause outbreaks and being of low incidence (EFSA 2007) tested negative for the nle genes.

The inventors have therefore shown that the simultaneous detection of the Shiga-toxins (stx1 and stx2), intimin (eae), together with some non-LEE effectors genes belonging to genomic O-island OI#71 and the module 2 of OI#122 provide a thorough approach for molecular risk assessment of STEC virulence.

In particular the process also comprises contacting said sample or DNA isolated therefrom with a pair of primers derived from at least one of the following target genes:
  ehxA using at least one primer defined by SEQ ID NO: 10 or SEQ ID NO: 11, or a fragment of at least fifteen nucleotides thereof;
  nleF using at least one primer defined by SEQ ID NO: 22 or SEQ ID NO: 23, or a fragment of at least fifteen nucleotides thereof;
  nleA using at least one primer defined by SEQ ID NO: 28 or SEQ ID NO: 29, or a fragment of at least fifteen nucleotides thereof.

The ehxA gene is present upon the plasmid pO157 frequently found in EHEC strains. The genes nleF (Z6020) and nleA (Z6024) issued from O-Island 71 PAI were unequally distributed in EHEC isolates and their prevalence was respectively of 72.76% and 79% that is much lower than the prevalence of nleH1-2 (Z6021) which was found to be absent in only one strain O26:H11 among the various strains tested by the inventors.

The amplification products according to the present invention can be generated using any suitable DNA amplification technique such as PCR either in simplex or multiplex forms, using any of the various natural or engineered enzymes available for this purpose. Alternative methods such as nucleic acid sequence-based amplification (NASBA), branched DNA, strand displacement amplification and the loop-mediated isothermal amplification (LAMP) method (Compton 1991, Chang 1991, Walker et al. 1992, Notomi et al. 2000) could also be used to generate the amplification products.

In particular the amplification products, when present, are detected using a degenerate probe defined by the following sequence for each target gene:
  stx1, SEQ ID NO: 3, or a fragment of at least fifteen nucleotides thereof;
  stx2, SEQ ID NO: 6, or a fragment of at least fifteen nucleotides thereof;
  eae, SEQ ID NO: 9, or a fragment of at least fifteen nucleotides thereof;
  espK, SEQ ID NO: 84, or a fragment of at least fifteen nucleotides thereof;
  ehxA, SEQ ID NO: 12, or a fragment of at least fifteen nucleotides thereof;
  nleF, SEQ ID NO: 24, or a fragment of at least fifteen nucleotides thereof;
  nleB, SEQ ID NO: 18 or SEQ ID NO: 81, or a fragment of at least fifteen nucleotides thereof;
  nleH1-2, SEQ ID NO: 27, or a fragment of at least fifteen nucleotides thereof;
  nleE, SEQ ID NO: 21, or a fragment of at least fifteen nucleotides thereof;
  nleA, SEQ ID NO: 30, or a fragment of at least fifteen nucleotides thereof;
  ent/espL2, SEQ ID NO: 15, or a fragment of at least fifteen nucleotides thereof.

In particular the process further comprises performing a negative amplification control and/or an inhibition control;
  and detecting the presence or the absence of an amplification product from said reactions.

In processes which concern aspects of human health, it is desirable as far as possible to ensure the results of the assay are as accurate and dependable as possible. In order to do this the assay may comprise a number of internal and external controls to ensure that the results of the assay are representative of the true contents of the sample. Therefore the present process may comprise a negative amplification control to ensure any detected products are true positives and also the process may comprise an inhibition control to ensure that the DNA from the sample is able to be amplified and hence that no false negatives are generated.

In addition to these types of internal experimental controls, the process may also be performed a number of times and the results pooled so as to achieve a more representative result.

In particular the probes are labelled with at least one fluorescent label.

Non-limiting examples of suitable fluorescent labels include 6-carboxylfluorescein (FAM), tetrachloro-6-carboxyfluorescein (TET), 6-carboxy-X-rhodamine (ROX). Non-limitative examples of suitable quenchers for labelling dual-labelled probes include 6-carboxy-tetramethyl-rhodamine (TAMRA), DABCYL, Non-Fluorescent Quenchers such as quenchers of the Black Hole Quencher family (BHQ), or including a minor groove binder group (MGB).

In particular wherein the amplification products are generated using a multiplex amplification reaction.

Alternatively the amplification products are generated using a series of independent/simplex amplification reactions.

In particular wherein the amplification reactions are performed in a macroarray.

In accordance with the present patent application a macroarray is used to describe a preformed structure such as a substrate upon which a number of DNA primers have been spotted, these primers being those described according to the various aspects of the present invention. Such a macroarray therefore allows the routine performance of one or more of the detection assays described herein. A preferred macroarray is the GeneDisc system described herein.

The inventors preferred means for performing the process is a GeneDisc array which allows the simultaneous testing of the genes encoding Shiga toxins 1 and 2 (stx1 and stx2), intimins (eae), enterohaemolysin (ehxA) and six different nle genes derived from genomic islands OI#71 and OI#122 (module 2).

The EHEC associated virulence determinants were reliably detected with the GeneDisc assay, presenting it as a suitable detection tool for routine diagnostics. In contrast to many other diagnostic tests, the results are obtained without need for special laboratory equipment and for specifically trained personnel and the assay is performed in a very short time. Such a low density macro-array would represent thus an innovative and efficient molecular risk assessment tool for routine monitoring of STEC isolates and for identification of classical and new emerging EHEC strains.

In particular wherein the amplification reaction is a real time PCR reaction. Real time PCR, also called quantitative real time polymerase chain reaction (qPCR) or kinetic polymerase chain reaction, is used to amplify and simultaneously quantify a targeted DNA molecule. It enables both detection and quantification (as absolute number of copies or relative amount when normalized to DNA input or additional normalizing genes) of a specific sequence in a DNA sample. The procedure follows the general principle of polymerase chain reaction; its key feature is that the amplified DNA is quantified as it accumulates in the reaction in real time after each amplification cycle (Mackay 2007). Two common methods of quantification are the use of fluorescent dyes that intercalate with double-strand DNA, and modified DNA oligonucleotide probes that fluoresce when hybridized with a complementary DNA (Mackay 2007).

A preferred RT-PCR method uses the GeneDisc system as outlined below.

According to a further aspect of the present invention there is provided a process to perform a molecular risk assessment upon a STEC strain, wherein said process is characterised in that it also comprises contacting said sample or DNA isolated therefrom with a pair of primers derived from at least one of the following target genes:

nleB using at least one primer defined by SEQ ID NO: 16, SEQ ID NO: 17, SEQ ID NO: 79 or SEQ ID NO: 80 or a fragment of at least fifteen nucleotides thereof;

nleH1-2 using at least one primer defined by SEQ ID NO: 25 or SEQ ID NO: 26, or a fragment of at least fifteen nucleotides thereof;

nleE using at least one primer defined by SEQ ID NO: 19 or SEQ ID NO: 20, or a fragment of at least fifteen nucleotides thereof;

ent/espL2 using at least one primer defined by SEQ ID NO: 13 or SEQ ID NO: 14, or a fragment of at least fifteen nucleotides thereof;

and detecting the presence or the absence of an amplification product for each of said target genes.

In addition to the specified primers, other primers to the specified target genes can also be used and are encompassed by this aspect of the present invention.

The present invention therefore also provides a process to perform a molecular risk assessment upon a sample known to comprise a STEC strain. Wherein the presence of the listed target genes indicates the STEC strain is likely to be an EHEC strain and hence hazardous to human health.

According to a further aspect of the present invention there is provided a method to predict the serotype of a STEC strain based upon the pattern of nle genes present in a sample. This method comprises the steps of:

contacting said sample or DNA isolated therefrom with a pair of primers derived from the following target genes:

nleB using at least one primer defined by SEQ ID NO: 16, SEQ ID NO: 17, SEQ ID NO: 79 or SEQ ID NO: 80 or a fragment of at least fifteen nucleotides thereof;

nleH1-2 using at least one primer defined by SEQ ID NO: 25 or SEQ ID NO: 26, or a fragment of at least fifteen nucleotides thereof;

nleE using at least one primer defined by SEQ ID NO: 19 or SEQ ID NO: 20, or a fragment of at least fifteen nucleotides thereof;

ent/espL2 using at least one primer defined by SEQ ID NO: 13 or SEQ ID NO: 14, or a fragment of at least fifteen nucleotides thereof;

nleF using at least one primer defined by SEQ ID NO: 22 or SEQ ID NO: 23, or a fragment of at least fifteen nucleotides thereof;

nleA using at least one primer defined by SEQ ID NO: 28 or SEQ ID NO: 29, or a fragment of at least fifteen nucleotides thereof;

and detecting the presence or the absence of an amplification product for each of said target genes.

The inventors have found that the pattern of nle genes present in a strain differs between different strains and hence can be used to distinguish between different EHEC strains.

One characteristic nle pattern [ent/espL2, nleB, nleE, nleF, nleH1-2, nleA] was found associated with EHEC O157:[H7], O111:[H8], O26:[H11], O103:[H25], O118:[H16], O121: [H19], O5:[$H_{NM}$], O55:[H7], O123:[H11], O172:[H25], and O165:[H25] strains. Interestingly, sorbitol-fermenting (SF) O157:[$H_{NM}$], stx2 strains and O-rough: [H7] (stx2, eae-gamma) strains, that were previously identified as positive for the rfb$E_{O157}$ gene showed the same typical virulence profile.

This approach can also be used to identify a number of new emerging EHEC strains that were recently reported as severe human pathogens. One of these is the EHEC O103:H25 type strain, responsible for a foodborne outbreak of HUS in Norway in 2006 (Schimmer et al. 2008), which had the same nle profile as EHEC O157:[H7], that is [ent/espL2, nleB, nleE, nleF, nleH1-2, nleA].

Another emerging EHEC type O5:$H_{NM}$ strain isolated from beef, dairy products and human patients with HC (McLean et al. 2005) shows the same nle pattern [ent/espL2, nleB, nleE, nleF, nleH1-2, nleA]. Interestingly, EHEC O118: H16/$H_{NM}$ currently emerging as a new highly virulent STEC type in Europe (Maidhof et al. 2002) shows this same nle pattern [en/espL2, nleB, nleE, nleF, nleH1-2, nleA] that is characteristic for EHEC O157:H7 and most of the typical EHEC strains tested.

Based on the PCR tests described in accordance with the invention, the inventors have found that not all EHEC possess a complete (all six nle target genes listed above) nle pattern. EHEC strains of serotypes O103:H2, O145:H28 showed a second characteristic nle pattern with positive signals for only [ent/espL2, nleB, nleE, nleH1-2] by using the primers and probes described in the invention. Using other primers or probes to detect the same genes may result in a totally different pattern. Thus, Creuzburg and Schmidt (2007) using different primers report the detection of nleA in some O103:H2 strains. They also report the existence of 11 different nleA variants in *E. coli* strains showing that the nleA like the other nle genes is likely genetically variable.

By using the primers and probes of the invention, other newly emerging EHEC O15:H2 and O45:H2, which are highly virulent clones involved in HUS, were found to possess the same nle pattern [ent/espL2, nleB, nleE, nleH1-2] as EHEC O103:H2 and O145:H28 strains.

The overall results indicate that EHEC constitute a heterogeneous group sharing a common core of nle virulence determinants but also harbour many variable nle genes that are strain and/or serotype specific, probably reflecting adaptation of these strains to different host or environmental niche. It is noteworthy that the presence in the same strain of a core of virulence determinants [eae, ent/espL2, nleB, nleE, and nleH1-2] is a strong signature of a pathogenic EHEC that can cause human morbidity and mortality. The inventors have shown that these virulence factors are found in all typical EHEC and also in new emerging EHEC types in Europe and North-America e.g. O5:$H_{NM}$ (McLean et al. 2005), O15:H2 (Starr et al. 1998), O118:H16 (Maidhof et al. 2002), O121: H19 (Brooks et al. 2005).

In particular therefore wherein the nle pattern is:

[ent/espL2, nleB, nleE, nleF, nleH1-2, nleA], the EHEC strain is likely to belong to the group comprising: EHEC O157:[H7], O111:[H8], O26:[H11], O118:[H16], O121: [H19], O5:[HNM], O55:[H7], O123:[H11], O172:[H25], O165:[H25], O157:[H$_{NM}$], O103:[H25], O5:[H$_{NM}$], O118: [H16/H$_{NM}$]; or

[ent/espL2, nleB, nleE, nleH1-2], the EHEC strain is likely to belong to the group comprising: EHEC O103:[H2], O145: [H28], O15:[H2] and O45:[H2].

In addition a number of stx-negative, eae-positive *E. coli* strains belong to EHEC associated serotypes which resemble EHEC strains according to their eae-genotypes and their nle-gene pattern. It seems likely that these strains represent remnants of EHEC strains that have lost their stx genes. Thus, the nle-genotyping assay could be helpful to detect remnants of EHEC in HUS-patients which were reported to excrete frequently EHEC that have lost their stx-genes with their faeces (Bielaszewska et al. 2007). The nle genes, in different distributions, were also detected in some EPEC strains (O113:H6, O127:H6, O128:H2, O156:H8, O55:H6, O55:H7, O84:H2 and O86:H40). Contrary to the results reported by Creuzburg and Schmidt (2007), the EPEC strain E2348169 (O127:H6) was tested positive for the nleA (Z6024) in our study. The fact that these EPEC strains carry multiple types of nle genes is a clear indication of the role these effectors might play in EPEC induced diarrhea in infants. These nle genes were absent in Enterobacteriaceae species that are frequently isolated from human feces and in fecal *E. coli* that represent the stool flora of healthy infants. That is another evidence that nle virulotyping is suitable for a rapid characterization of highly virulent Stx-positive *E. coli* strains.

In accordance with a further aspect of the present invention there is provided a kit for the detection of shiga toxin producing organisms, comprising at least a set of primers for the target genes:
nleB;
nleH1-2;
nleE;
ent/espL2;
and optionally a set of probes as to detect the amplification products for each target gene.

In accordance with a further aspect of the present invention there is provided an isolated nucleic acid molecule consisting of the amplification product resulting from a process according to the present invention.

In accordance with a second aspect of the present invention there is provided a process to perform a molecular risk assessment (MRA) upon a sample suspected to contain a Shiga toxin-encoding *Escherichia coli* (STEC), comprising the steps:

a) contacting said sample or DNA isolated therefrom with a pair of primers derived from the following target genes:
stx1;
stx2; and at least one of the following target genes:
eae;
espK;
and with a pair of primers derived from at least one of the following target genes:
nleB;
nleH1-2;
nleE;
ent/espL2;
and detecting the presence or the absence of an amplification product for each of said target genes; and if the amplification products are detected then:

b) contacting said sample or DNA isolated therefrom with one or more pairs of primers derived from the eae target gene and determining the eae subtype.

In accordance with a preferred aspect of the present invention in step a) the presence of the genes stx1, stx2, eae or espk and either nleB or ent/espL2 is determined.

In accordance with a further preferred aspect of the present invention the presence of the specific nleB2 allele of the nleB gene is detected in this assay using at least one primer selected from the group SEQ ID NO: 79 or SEQ ID NO: 80 or a fragment of at least fifteen nucleotides thereof. The product of such an amplification reaction being detected using a probe consisting of SEQ ID NO: 81 or a fragment of at least 15 nucleotides thereof. The inventors have in particular established a link between the presence of the nleB2 allele and the host strain being an EHEC rather than a EPEC.

The eae gene encodes a number of distinct subtypes of which currently 21 are known and a smaller number are routinely found in samples. These eae genotypes can be routinely distinguished on the basis of their sequence using a PCR reaction (Nielsen and Andersen 2003), as well as by other means such as sequencing, southern hybridisation and other types of amplification reaction.

In accordance with a further aspect of the present invention in the step b), the eae subtypes eae γ, eae β, eae θ, and eae ε are detected.

According to a further aspect of the present invention the eae subtype is determined by a method which comprises the steps of:
contacting said sample or DNA isolated therefrom with a pair of primers derived from the following target genes:
eae γ using at least one primer defined by SEQ ID NO: 52 or SEQ ID NO: 53, or a fragment of at least fifteen nucleotides thereof;
eae β using at least one primer defined by SEQ ID NO: 49 or SEQ ID NO: 50 or a fragment of at least fifteen nucleotides thereof;
eae θ using at least one primer defined by SEQ ID NO: 64 or SEQ ID NO: 65, or a fragment of at least fifteen nucleotides thereof;
eae ε using at least one primer defined by SEQ ID NO: 58 or SEQ ID NO: 59, or a fragment of at least fifteen nucleotides thereof;
and detecting the presence or the absence of an amplification product for each of said target genes.

These reactions could in particular be real time PCR reactions in which case probes for amplification products of each of eae γ, eae β, eae θ and eae ε could be detected using probes defined by SEQ ID NO: 54 for eae γ, SEQ ID NO: 51 for eae β, SEQ ID NO: 66 for eae θ and SEQ ID NO: 60 for eae ε.

In addition the detection of other eae subtypes is also encompassed by the present invention such as eae α and eae ζ using at least one primer defined by SEQ ID NO: 46 or SEQ ID NO: 47, or a fragment of at least fifteen nucleotides thereof for eae α and/or using at least one primer defined by SEQ ID NO: 61 or SEQ ID NO: 62, or a fragment of at least fifteen nucleotides thereof for eae ζ.

Again such detection reactions are preferably realtime PCR reactions in which case probes defined by SEQ ID NO: 48 for eae α and SEQ ID NO: 63 for eae ζ, could be used respectively.

The inventors have found there to be a correlation between the subtype of the eae gene and certain seropathotypes (or serogroups) in EHEC strains. The presence therefore of the stx1/2 and eae genes and selected nle gene(s) (e.g. nleB) together with a certain eae subtype and serotype is strongly indicative that the tested sample comprises an EHEC strain.

In accordance with the present invention a serogroup or seropathotype is a group of bacteria containing a common antigen.

Although a STEC may belong to one of a number of serogroups, those most firmly associated with severe human disease, such as EHEC strains, generally belong to the serogroups O157:[H7], O111:[H8], O26:[H11], EHEC O103: [H2], O145:[H28] (EFSA, 2007). The genes which correspond to these serogroups are rfbE (O157), wbdl (O111), wzx (O26), ihp1 (O145) and wzx (O103).

It is possible to test a strain for the presence of one or more of the antigens which define these serogroups and therefore in accordance with a further aspect of the preset invention the process according to this second aspect of the present invention further comprises contacting said sample or DNA isolated therefrom with a pair of primers derived from the following target genes:
rfbE (O157);
wbdl (O111);
wzx (O26);
ihp1 (O145);
wzx (O103).

According to a further aspect of the present invention the serotype is determined by a method which comprises the steps of:
contacting said sample or DNA isolated therefrom with a pair of primers derived from the following target genes:
rfbE (O157) using at least one primer defined by SEQ ID NO: 31 or SEQ ID NO: 32, or a fragment of at least fifteen nucleotides thereof;
wbdl (O111) using at least one primer defined by SEQ ID NO: 34 or SEQ ID NO: 35, or a fragment of at least fifteen nucleotides thereof;
wzw (O26) using at least one primer defined by SEQ ID NO: 37 or SEQ ID NO: 38, or a fragment of at least fifteen nucleotides thereof;
Ihp1 (O145) using at least one primer defined by SEQ ID NO: 40 or SEQ ID NO: 41, or a fragment of at least fifteen nucleotides thereof;
wzx (O103) using at least one primer defined by SEQ ID NO: 43 or SEQ ID NO: 44, or a fragment of at least fifteen nucleotides thereof;
and detecting the presence or the absence of an amplification product for each of said target genes.

These reactions could in particular be real time PCR reactions in which case probes for amplification products of each of rfbE (O157), wbdl (O111), wzx (O26), ihp1 (O145) and wzx (O103) could be detected using probes defined by SEQ ID NO: 33 for rfbE (O157), SEQ ID NO: 36 for wbdl (O111), SEQ ID NO: 39 for wzx (O26), SEQ ID NO: 42 for Ihp1 (O145) and SEQ ID NO: 45 for wzx (O103).

It is also possible to detect other serotypes such as O118: [H16], O121:[H19], O5:[HNM], O55:[H7], O123:[H11], O172:[H25], O165:[H25], O157:[$H_{NM}$], O103:[H25], O5: [$H_{NM}$], O118:[H16/$H_{NM}$], O15:[H2] and O45:[H2] and the detection of one or more of these serotypes is also encompased by the present patent application.

According to a further aspect of the present invention the serotype is determined by a method which comprises the steps of:
contacting said sample or DNA isolated therefrom with a pair of primers derived from the following target genes:
wzx (O121) using at least one primer defined by SEQ ID NO: 67 or SEQ ID NO: 68, or a fragment of at least fifteen nucleotides thereof;
wzy (O118) using at least one primer defined by SEQ ID NO: 70 or SEQ ID NO: 71, or a fragment of at least fifteen nucleotides thereof;
wzx (O45) using at least one primer defined by SEQ ID NO: 73 or SEQ ID NO: 74, or a fragment of at least fifteen nucleotides thereof;
wbgN (O55) using at least one primer defined by SEQ ID NO: 76 or SEQ ID NO: 77, or a fragment of at least fifteen nucleotides thereof;
and detecting the presence or the absence of an amplification product for each of said target genes.

These reactions could in particular be real time PCR reactions in which case probes for amplification products of each wzx (O121); wzy (O118); wzx (O45); wbgN (O55) could be detected using probes defined by SEQ ID NO: 69 for wzx (O121), SEQ ID NO: 72 for wzx (O118), SEQ ID NO: 75 for wzx (O45), SEQ ID NO: 78 for wbgN (O55).

Therefore in accordance with a preferred embodiment of this second aspect of the present invention there is provided an assay comprising the steps:
a) contacting said sample or DNA isolated therefrom with a pair of primers derived from the following target genes:
stx1;
stx2;
eae;
espK;
nleB or ent/espL2;
rfbE (O157);
and detecting the presence or the absence of an amplification product for each of said target genes; and if the amplification products are detected then:
b) contacting said sample or DNA isolated therefrom with one or more pairs of primers derived from the following target genes and/or eae subtype:
eae γ;
eae β;
eae θ;
eae ε;
wbdl (O111);
wzx (O26);
ihp1 (O145);
wzx (O103).

There will now be described by way of example a specific mode contemplated by the Inventors. In the following description numerous specific details are set forth in order to provide a thorough understanding. It will be apparent however, to one skilled in the art, that the present invention may be practiced without limitation to these specific details. In other instances, well known methods and structures have not been described so as not to unnecessarily obscure the description.

EXAMPLE 1

Materials and Methods

Principle of the GeneDisc Array

The principle of the GeneDisc array (GeneSystems, Bruz, France) has been previously reported (Beutin et al. 2009). It is based on real-time PCR applications of multiple targets in a plastic reaction tray engraved with reaction microchambers preloaded with desiccated PCR primers and TaqMan® probes labeled either with the reporter dye 6-FAM (490-520 nm) or ROX (580-620 nm).

Properties of the GeneDisc Array Developed in this Study

The "virulotyping GeneDisc" is designed for simultaneous examination of six different samples, each being tested for ten EHEC specific gene targets, and together with negative and inhibition controls. It has the following settings: microwell 1) negative PCR control (6-FAM label) and PCR inhibition control (ROX-label), microwell 2) stx2 (FAM) and stx1 (ROX), microwell 3) ent/espL2 (FAM) and nleF (ROX), microwell 4) nleB (FAM) and nleH1-2 (ROX), microwell 5) nleE (FAM) and nleA (ROX), and microwell 6) ehxA (FAM) and eae (ROX).

For further experiments on eae subtype detection and serotype detection the following settings were used in experiment 1: microwell 1) O157 (FAM) and stx1+stx2 (ROX); microwell 2) nleB (FAM) and eae (ROX); microwell 3) negative control (FAM and inhibition control (ROX). In experiment 2: microwell 1) eaeγ (FAM) and O113 (ROX); microwell 2) O26 (FAM) and O111 (ROX); microwell 3) O145 (FAM) and eaeβ (ROX); microwell 4) eaeθ (FAM) and eaeε (ROX); microwell 5) negative control (FAM) and inhibition control (ROX).

The oligonucleotide primers and gene probes used in the GeneDisc are described in Table 1. Primers and probes used for detecting stx1, stx2, eae and ehxA were described previously (Nielsen and Andersen 2003, Perelle et al. 2004) and were evaluated in the "VTEC Screening" GeneDisc in a recent study (Beutin et al. 2009). All oligonucleotides were purchased from Sigma-Aldrich (St. Quentin Fallavier, France). GeneDisc spotting and manufacturing were performed by GeneSystems (Bruz, France).

In Table 1 the sequence of oligonucleotides Y is (C, T), S is (C, G), W is (A, T), R is (A, G), M is (A, C). K is (G, T); H is (A,T,C); and D is (G,A,T); FAM=6-carboxylfluorescein; ROX=carboxy-X-rhodamine; probe=either FAM or ROX; BHQ=Black Hole Quencher. * complementary strand; a: gene encoding Shiga-toxin 1; b: gene encoding Shiga-toxin 2; c: gene encoding intimin; d: gene encoding enteroharemolysin; e: gene encoding the "putative non LEE effector ent/ espL2"; f: gene encoding the "putative non LEE effector B"; g: gene encoding the "putative non LEE effector E"; h: gene encoding the "putative non LEE effector F"; I: gene encoding the "putative non LEE effector H1-2"; gene encoding the "putative non LEE effector A".

Bacterial Strains Investigated with the GeneDisc Array

Strains of E. coli and other Enterobacteriaceae that were investigated for their virulence gene content with the "virulotyping GeneDisc" were from the collection of the National Reference Laboratory for E. coli at the Federal Institute for Risk Assessment (BfR) in Berlin, Germany; and from the French Food Safety Agency (AFSSA) in Maisons-Alfort, France. For evaluation we used STEC reference strains and eae-positive "Attaching and Effacing E. coli" (AEEC) that were previously characterized for their stx- and eae-genotypes (Beutin et al. 2007, Kozub-Witkowski et al. 2008). For reference strains of EHEC O-groups O26, O103, O111, O145 and O157 we used strains previously identified by serotyping of their O- and H-antigens and by fliC genotyping (Beutin et al. 2004). The characteristics and origin of EHEC reference strains H19 (O26:H11), PMK5 (O103:H2), CL37 (O111:[H8]), CB7874 (O145:[H28]) and EDL933 (O157:H7) that served as reference had been described in other publications (Beutin et al. 2004, Oswald et al. 2000, Tarr and Whittam 2002). The reference STEC strain EDL933 (O157:H7) and EPEC strain E2348/69 (O127:H6) were used as positive controls for testing the complete set of nle genes i.e. ent/espL2 (Z4326), nleB (Z4328), nleE (Z4329), nleF (Z6020), nleH1-2 (Z6021) and nleA (Z6024). Strain C600 (E. coli K-12) was taken as a negative control for all genes investigated in this work (Beutin et al. 2007). In addition, 68 enterobacteriaceal strains (C. sakasaki, Yersinia, Escherichia, Salmonella, Shigella, Citrobacter, Hafnia, Kebsiella, Proteus) that were characterized by standard methods (Ewing 1986) were used for evaluation of the GeneDisc array. Except for S. dysenteriae type 1 (stx1), the S. sonnei strain CB7888 (stx1) (Beutin et al. 2007) and the Citrobacter rodentium strain 10835 (eae), all other Enterobacteriacae isolates were negative for stx- and eae-genes. For examination, bacteria were cultured to single colonies on Luria-Broth Plates and grown overnight at 37° C. A small aliquot of the colony corresponding to approx. $2 \times 10^6$ bacteria was either DNA extracted using the InstaGene matrix (Bio-Rad Laboratories, Marnes La Coquette, France) or directly dissolved in 200 μl sterile water and vortexed thoroughly. 36 μl of the resuspended bacteria or DNA extracts were tested by the GeneDisc array.

EXAMPLE 2

Results

Association of eae-Types, ehxA Gene and nle Genes with Typical and Atypical EHEC Strains:

250 EHEC strains including typical EHEC (n=178), atypical EHEC (n=26), and new emerging EHEC strains (n=46) as well as stx-negative strains belonging to the same serotype as the EHEC strains (n=65) were investigated with the virulotyping GeneDisc array (Tables 2, 3 and 4). All EHEC strains were tested positive for either stx1 and/or stx2 genes giving a total concordance with data previously published (Beutin et al. 2004, Beutin et al. 2009, Fach et al. 2001, Perelle et al. 2004). Eae genes were detected in the strains belonging to the classical EHEC groups O26, O103, O111, O145 and O157 as well as in emerging EHEC type O5, O15, O45, O55, O118, O121, O123, O165, and O172 strains. Only one EHEC O103: H2 strain tested negative with the eae genes (Table 2).

Eae-genes were absent in all other STEC investigated including atypical EHEC O91:H21 and O113:H21, the latter are frequently isolated from food and from human patients (Werber et al. 2008). Remarkably, all eae-negative STEC as well as the atypical EHEC stains were also negative for the set of nle genes investigated in this study (Table 4).

In Table 4, the following abbreviations are used: EHEC is enterohaemorrhagic E. coli; STEC is Shiga toxin-producing E. coli; ETEC is enterotoxigenic E. coli; FEC is E. coli isolated from feces of healthy children, EC is E. coli.

nle genes encoded by islands OI#71 and OI#122 were present in typical EHEC strains including the new emerging serotypes. One characteristic pattern of nle genes (ent/espL2, nleB, nleE, nleF, nleH1-2 and nleA) was found in EHEC strains belonging to serotypes O157:[H7], O111:[H8], O26: [H11], O103:H25, O118:[H16], O121:[H19], O5:NM, O55: H7, O123:H11, O172:H25, and O165:H25 (Table 2). Among the 76 EHEC O157:[H7] strains, six were sorbitol-fermenting (SF) O157:$H_{NM}$, stx2 strains, these showed the same nle pattern as the non-SF O157:[H7] strains. Two O-rough: [H7] (stx2, eae-gamma) strains, previously identified as positive for the rfbE$_{O157}$ gene had the same nle pattern as serologically typable O157:[H7] strains.

Another type of nle pattern was found with EHEC strains belonging to serotypes O103:H2, O145:[H28], O45:H2, and O15:H2 strains. These were positive for all nle-genes investigated except for OI#71 encoded genes nleA and nleF (Table 2). Our results indicate that typical EHEC strains are highly conserved for the distribution of nle-genes and point to an association of eae-genotype, nle-pattern and serotype. Exceptions were rarely observed, such as absence of the nleH1-2 gene in one of the 34 examined EHEC O26:H11 strains (Table 2). Most (93.25%) of the typical EHEC strains were positive for the plasmid located ehxA gene encoding enterohemolysin, this marker was also present in 87% of new emerging EHEC, 73% of the atypical EHEC and in 42.66% of the other STEC strains investigated in this study.

Identification and Characterization of stx-Negative Strains Resembling EHEC for Serotype and Other Properties:

It was previously reported that EHEC strains can lose their stx-gene spontaneously during infection and upon subculturing (Friedrich et al. 2007). We were interested to investigate Stx-negative, eae-positive *E. coli* strains belonging to EHEC associated serotypes for their similarity with EHEC strains in regard to their eae-genotypes and their nle-genes. The results obtained with 65 strains are presented in Table 3. The inventors could identify three stx-negative O157:[H7], ten O26:[H11], one O103:[H2], three O121:[H19], one O121:[H-], four O55:H7 and one O15:H2 strains that showed similar eae-genotypes and nle patterns as stx-producing EHEC belonging to the same serotypes (Table 3). It seems likely that these strains represent remnants of EHEC strains belonging to these serotypes that have lost their stx-genes. In contrast, a group of fourteen O157 strains with non H7-flagellae ($H_{NT}$, H16, H2, H26, H27, H39, H45) was different from EHEC O157:H7 not only by their H-types but also by the eae-genotypes and absence of most nle genes investigated, except nleH1-2 and nleA.

EHEC O111:[H8] strains were usually positive for eae-theta and for all OI#71 and OI#122 encoded nle genes. Only one of 24 strains was negative with nleF (Table 2). Two single stx-negative O111:H11 strains (eae-beta) showed the same nle profile as EHEC O111:[H8] indicating that transfer of pathogenicity islands might have occurred between different pathogroups of *E. coli*. Interestingly, EPEC O111:H2 strains that cause gastroenteritis in infants were found different from EHEC O111:[H8], by their H-type, and by absence of OI#71 encoded nleF and nleA genes (Table 3). An EPEC O111:H19 strain (eae-eta) was even more distant from EHEC O111:[H8] since it carried none of the nle genes.

EHEC O145:[H28] strains are characterized by possession of the complete set of OI#122 module 2 encoded nle genes ent, nleB and nleE (Table 2). Interestingly, these genes were absent in two stx-negative O145:[H28] strains which resemble O145:[H28] EHEC for all other traits that were investigated (Table 3). It is possible that these strains are remnants of EHEC O145:[H28] which have lost their six genes and the OI#122 PAI. All EPEC O145 strains (O145:H34, O145:H4 and O145:Hr) differed significantly from EHEC O145:[H28] as they do not possess any nle gene and encode other eae-genotypes.

In the group of O103:H2 strains, the rabbit EPEC strain E22 was similar to all EHEC O103:H2 strains for the set of nle genes but differed by the eae-beta subtype as EHEC O103:H2 encode eae-epsilon. In contrast, the EHEC O103:H25 strain which caused an outbreak of HUS in Norway in 2006 (Schimmer et al. 2008) was found different from the classical EHEC O103:H2 clone by its H-type, eae-type and the set of nle genes.

We additionally investigated representatives of classical EPEC groups. The EPEC O55:H7 strain was similar for its eae-genotype and nle-genes to EHEC O157:[H7] strains. All nle genes investigated were also present in EPEC O127:H6, strain E2348/69. EPEC O84:H2 harbored all nle genes except nleE. EPEC O156:H8 was negative only for the OI#71 nleF and nleA genes. EPEC O128:H2 and O113:H6 were only positive for nleH and lacked the OI#122 module 2 associated nle genes. EPEC O55:H6 also lacked the OI#122 module 2 associated nle genes but carried nleH and nleF. In contrast EPEC O86:H40 carried the OI#122 module 2 encoded nle genes but none of those located on OI#71 (Table 3). Some other EPEC strains (O125:H6, O126:H6, O51, and O76:H51) did not possess any nle gene and usually encoded eae-alpha genotype. These findings pointed to significant differences between EPEC and EHEC strains, not only for their serotypes, but also for their LEE and non LEE associated effectors.

Identification and Characterisation of eae- and nle-Negative Strains.

Numerous types of STEC are isolated from animals and food but only 5% of these are positive for an eae-gene or belong to the typical EHEC serogroups O26, O103, O111, O145 and O157 (Beutin et al. 2007). Some of the eae-negative STEC strains are known to cause diarrhea in humans but are rarely involved in hemorrhagic diseases such as HC and HUS (Beutin et al. 2004, Friedrich et al. 2007, Werber et al. 2008). We were interested to investigate representative strains of the eae-negative STEC types that are frequently isolated from food (O8, O91, O100, O113, O146, O128 and O174). A total of 150 STEC strains that were isolated from food, animals and humans as well as 29 fecal *E. coli* isolates from healthy children (FEC) were investigated with the virulotyping Gene-Disc. The results are summarized in Table 4. None of the eae-negative STEC strains or of the FEC from healthy infants was positive for any of the nle genes, pointing to a close association between presence of the LEE and OI#122 and OI#71 encoded nle genes.

In order to examine the possible spread of the OI#122 and OI#71 encoded nle genes to other Enterobacteriaceae we have investigated 68 strains of bacteria comprising *Escherichia, Cronobacter, Yersinia, Salmonella, Shigella, Citrobacter, Hafnia, Kebsiella* and *Proteus* species. Except for the two strains of *S. dysenteriae* type 1 (stx1), the *S. sonnei* strain CB7888 (stx1) and the *Citrobacter rodentium* strain CB10835 (eae, nleE, nleA) (data not shown), all other Enterobacteriacae isolates were confirmed negative for the genes stx1 and/or stx2, eae, ehxA and for the nle genes (Table 4). In summary, these results show that the virulotyping array which combines the detection of the nle genes in association with the stx and eae genotypes is a suitable tool for a rapid identification of human virulent EHEC strains belonging to known and new emerging serotypes in samples which may contain other STEC, EPEC, other Enterobacteriaceae and human fecal *E. coli* flora.

A Molecular Risk Assessment Approach for Screening EHEC in Complex Matrices Based Upon a Multifaceted Analysis of eae Subtype and Serotype:

As explained above EHEC are an important existing and emerging group of foodborne pathogens representing a serious threat to food safety. No single genetic marker is known whose detection indicates the presence of EHEC in a complex poly-microbial sample (e.g. food or fecal samples) in a similar way to assays for other common microbial food contaminants such as *Salmonella* spp. Consequently, the rapid and simultaneous detection of several genetic markers in a multi-parametric assay is the most well-suited approach to the rapid screening of samples as a means to perform a molecular risk assessment which in turns allows more the resources needed to further study the suspect strain for instance by means of serotype specific enrichment culture.

The inventors have developed a first assay set out above based upon the detection of a minimum complement of genes, which is indicative that a STEC strain may also be an EHEC strain.

This assay can be further elaborated by also determining the subtype of the eae gene present in the sample.

The inventors have established that when the stx1/2, eae genes and at least one of the nle (ent/espL2, nleB, nleE, nleH1-2) genes is detected and when in a second step one of the specific eae subtypes, eae-γ, eae-β, eae-ε and eae-θ, are also detected; this can be used to predict the serotype of the EHEC strain (this of course can be further verified by detecting the presence of the gene underlying the serotype).

These correlations between eae subtype and serotype are as follows:
- EHEC O157:H7 and O145:H28 are suspected in particular when eae-γ, ent/espL2, nleB, nleE, and nleH1-2 are detected.
- EHEC O103:H2 is suspected in particular when eae-ε, ent/espL2, nleB, nleE, and nleH1-2 are detected.
- EHEC O26:H11 is suspected when eae-β, ent/espL2, nleB, nleE, and nleH1-2 are detected.
- EHEC O111 is H11 is suspected when eae-θ, ent/espL2, nleB, nleE, and nleH1-2 are detected.

In a complex sample the unique presence of nle genes is not always indicative of the presence of an EHEC in this sample. It may result for example of the presence of EPEC or *Citrobacter rodentium* which have also the nle genes. In comparison the, the simultaneous detection of the genes stx (stx1, stx2), eae (in particular subtypes γ, β, ε and θ) together with at least one of the nle genes (ent/espL2, nleB, nleE, nleH1-2) is a much more clear signature of virulence and a strong signal of EHEC contamination.

The inventors have also developed a further two step process to determine the risk presented by any *E. coli* spp. present in a sample and in particular to determine whether the sample comprises an EHEC strain.

In a first step, the presence of the stx1/2 and eae genes is determined as well as at least one of the ent/espL2, NleB, NleE and NleH1-2. This first step can be performed using the oligonucleotides described in Table 1 below.

This first step allows a worker to determine if the sample comprises at least the essential genes for an EHEC strain. If one or more of these genes is not present the sample can be considered as presenting a low risk and hence does not need to be studied further.

If all these genes are present, the sample does present a risk and a second step is then performed in which at least the eae subtype (such as eae-γ, eae-β, eae-ε and eae-θ) and the presence of one or more serotype genes (such as serotypes O157, O103, O26, O111, O145) is also determined.

With this combined set of data, a worker can determine whether the sample potentially comprises an EHEC strain and hence needs to be removed from the supply chain (in the case of a food sample) and/or retained for further study.

Based on the invention, the following multi-parametric approach allows the reliable screening of EHEC in complex samples.

The correlations that the inventors have found are summarised below in Tables 2 and 5.

The inventors have also tested a number of other less frequently observed serotypes from emerging EHEC strains (in total 46 strains) and have found further correlations between eae subtype and nle gene complement with these other serotypes, see Tables 2 and 6.

In accordance with this aspect of the invention the inventors provide a two step process as follows:
a) contacting the sample or DNA isolated therefrom with a pair of primers derived from the following target genes:
  stx1;
  stx2;
  eae;
  nleB or ent/espL2;
  rfbE (O157);
and detecting the presence or the absence of an amplification product for each of the target genes; and if the amplification products are detected then:
b) contacting the sample or DNA isolated therefrom with one or more pairs of primers derived from the following target genes and/or eae subtype:
  eae γ;
  eae β;
  eae θ;
  eae ε;
  wbdl (O111);
  wzx (O26);
  ihp1 (O145);
  wzx (O103);
and detecting the presence or the absence of an amplification product for each of the target genes.

The data from this assay can be compared with the correlations between eae subtype and serotype, in a strain which also comprises the essential virulence genes (e.g. stx1/2, eae and nleB or ent/espL2) and an informed and reproducible decision can be made about the risk that the sample poses.

The Presence of EHEC- and EPEC-Associated Genetic Markers in Strains of *E. coli* and Association with nleB Alleles A set of *E. coli* strains, all characterized as stx-negative and eae-positive were further analyzed for the presence of the genes espK and nleB and these were compared with a number of EHEC strains which were stx-positive and eae-positive.

The nleB gene was found to be diverse and different alleles exist. The inventors therefore selected two sets of primers and probes, identifying two different nleB alleles which were found unequally distributed in EPEC and EHEC strains (Table 7).

Remarkably, all EHEC strains tested positive for both nleB and nleB2 genotypes as well as for espK. Only very few EPEC strains, which differ clearly in their serogroups from typical EHEC strains, harbor the complete set of [nleB, nleB2 and espK] genetic markers.

The other EPEC strains which divided into several groups based upon their nleB genotype and the presence of the espK gene were never found positive for the complete set of [nleB, nleB2 and espK].

Interestingly, some EPEC strains lack the nleB2 gene sequence or had an nleB2 sequence significantly different so that they were not detected with the PCR test specific for nleB2. Also, some EPEC strains gave a very weak signal with the nleB2 PCR test, indicating the presence in these strains of an nleB2 gene sequence variant. (In regards to the high Ct value generated with the PCR test described in the invention with some EPEC strains, such strains were reported as nleB2-negative in the Table 7).

In accordance with the present invention the Ct (cycle threshold) is defined as the number of cycles required for the fluorescent signal to cross the threshold (i.e. exceeds background level). Ct levels are inversely proportional to the amount of target nucleic acid in the sample (i.e. the lower the Ct level the greater the amount of target nucleic acid in the sample and/or conversely the high Ct value generated with the PCR test described in the invention with some EPEC strains either indicates a low amount of target DNA or an inefficient replicative phase in the PCR reaction).

As a consequence of the above, detection of the nleB2 gene sequence was mainly restricted to EHEC O157, O145, O103, O111, O26 and O121. Therefore the detection of this specific sequence in a strain or in a poly-microbial sample correlates with the presence of EHEC of the Top 5 and to a limited number of EPEC strains (see Table 7).

The detection of the nleB2 and espK gene sequences in the same *E. coli* strain or in the same sample reinforces the EHEC predictive value (see Table 7). The restriction of these two sequences in EHEC and in a very limited number of non EHEC strains is a great value as part of a molecular risk assessment for EHEC strains.

The genes stx1, stx2, eae, nleB and espK when detected by themselves are not sufficient to predict the presence of EHEC in a complex poly-microbial sample (e.g. food or fecal samples). In food samples (such as dairy products, beef) the detection of one of these genes taken individually is not enough to suspect that a sample is contaminated by an EHEC strain. This is because a number of foods, which are not contaminated by EHEC, carry one or more *E. coli* spp that do comprise at least one of these genes, they cannot therefore be used by themselves as a selective marker for the detection of an EHEC. However, when all these genes are detected or associated in the same sample they can be used as a signature of virulence as demonstrated by the data presented herein.

Also based upon the data presented in Table 7, to further enhance the molecular risk assessment methods the detection of the eae gene can be advantageously replaced or supplemented with the detection of the espK gene. In addition detection of the nleB gene could be advantageously detected based on the nleB2 sequence. Both these elaborations of the molecular risk assessment according to the present invention increase the level of information provided by the assessment and so allow a more robust assessment of the risk associated with a sample to be made.

TABLE 1

Primers and probes preloaded in the GeneDisc.

| Target gene sequence | Forward primer, reverse primer and probe sequences (5'-3') | Location within sequence | GenBank accession number | Reference |
|---|---|---|---|---|
| stx1[a] | TTT GTY ACT GTS ACA GCW GAA GCY TTA CG | 878-906 | M16625 | (Perelle et al. 2004) |
| | CCC CAG TTC ARW GTR AGR TCM ACR TC * | 983-1008 | | |
| | ROX- CTG GAT GAT CTC AGT GGG CGT TCT TAT GTA A -BHQ | 941-971 | | |
| stx2[b] | TTT GTY ACT GTS ACA GCW GAA GCY TTAC G | 785-813 | X07865 | (Perelle et al. 2004) |
| | CCC CAG TTC ARW GTR AGR TCM ACR TC * | 887-912 | | |
| | FAM- TCG TCA GGC ACT GTC TGA AAC TGC TCC -BHQ | 838-864 | | |
| eae[c] | CAT TGA TCA GGA TTT TTC TGG TGA TA | 899-924 | Z11541 | (Nielsen and Andersen 2003) |
| | CTC ATG CGG AAA TAG CCG TTA * | 979-1000 | | |
| | ROX- AT AGT CTC GCC AGT ATT CGC CAC CAA TAC -BHQ * | 936-966 | | |
| ehxA[d] | GTG TCA GTA GGG AAG CGA ACA | 41832-41852 | AF074613 | This study |
| | ATC ATG TTT TCC GCC AAT G * | 41939-41957 | | |
| | FAM- CGT GAT TTT GAA TTC AGA ACC GGT GG -BHQ | 41868-41893 | | |
| ent/espL2[e] | TCC TGG ATT ATT TTC TGC ATT TCA | 3929758-3929781 | AE005174 | This study |
| | ACT ATT GCC AAG TAC GCC ACA A* | 3929833-3929812 | | |
| | FAM-AAT GGT CAT GCA GAC GCA ATA AAG GCA TA-BHQ | 3929783-3929811 | | |
| nleB[f] | CAT GTT GAA GGC TGG AAS TTT GT | 3931502-3931524 | AE005174 | This study |
| | CCG CTA CAG GGC GAT ATG TT* | 3931573-3931554 | | |
| | FAM-ACA GAG ACG GGA AAA ACT GGA TGC CA-BHQ | 3931527-3931552 | | |
| nleE[g] | AGA AGC GTT TGA ACC TAT TTC CA | 3932207-3932229 | AE005174 | This study |
| | TTG GGC GTT TTC CGG ATA T* | 3932289-3932271 | | |
| | FAM-AGC CAG TAC ACC GGA AGG AAG CTG G-BHQ | 3932237-3932261 | | |
| nleF[h] | TGA GGT GAG AAA TGA AAA TAC TGA TG* | 2281256-2281231 | AE005174 | This study |
| | CTA TCC CTG TCC TCT ATC GTC ATTC | 2281182-2281206 | | |
| | ROX-TGT CGG AGC GCT GAG GGC G-BHQ* | 2281226-2281208 | | |
| nleH1-2[i] | ACA AGA GAA AGT CAT AGT GGT TG | 2282298-2282276 | AE005174 | This study |
| | AAT CTC YCC CTT AGG CCA TCC CA* | 2282230-2282252 | | |
| | ROX-TTT ACT AAT CTG TTG CAC AGG-BHQ | 2282274-2282254 | | |

TABLE 1-continued

Primers and probes preloaded in the GeneDisc.

| Target gene sequence | Forward primer, reverse primer and probe sequences (5'-3') | Location within sequence | GenBank accession number | Reference |
|---|---|---|---|---|
| nleA[j] | AGA TAA CYC TAA TAC TAA ATA TGC C | 2285138-2285162 | AE005174 | This study |
| | GCC CAA CCA TTG CRC CGA TAT GAG G* | 2285274-2285250 | | |
| | ROX-TTC CCA ATG CTG CCG CAA ATG CGC BHQ | 2285164-2285190 | | |
| rfbE (O157) | TTTCACACRRARRGGATGGTCTCAA | 348-372 | AF163329 | This Study |
| | CGATGAGTTTATCTGCAAGGTGAT | 412-435 | | |
| | Probe-AGGACCGCAGAGGAAAGAGAGGAATTAAGG | 381-410 | | |
| wbdI (O111) | CGAGGCAACACATTATATAGTGCTTT | 3464-3489 | AF078736 | This Study |
| | TTTTTGAATAGTTATGAACATCTTGTTTAGC | 3579-3609 | | |
| | Probe-TTGAATCTCCCAGATGATCAACATCGTGAA | 3519-3548 | | |
| wzw (O26) | CGCGACGGCAGCGAAAATT | 5648-5666 | AF529080 | This Study |
| | AGCAGGCTTTTATATTCTCCAACTTT | 5757-5782 | | |
| | Probe-CCCCGTTAAATCAATACTATTTCACGAGGTTGA | 5692-5724 | | |
| Ihp1 (O145) | CGATAATATTTACCCCACCAGTACAG | 1383-1408 | AF531429 | This Study |
| | GCCGCCGCAATGCTT | 1500-1514 | | |
| | Probe-CCGCCATTCAGAATGCACACAATATCG | 1472-1498 | | |
| wzx (O103) | CAAGGTGATTACGAAAATGCATGT | 4299-4323 | AY532664 | This Study |
| | GAAAAAAGCACCCCCGTACTTAT | 4397-4375 | | |
| | Probe-CATAGCCTGTTGTTTTAT | 4356-4373 | | |
| wzx (O121) | TGG TCT CTT AGA CTT AGG GC | 6849-6868 | AY208937 | This Study |
| | TTA GCA ATT TTC TGT AGT CCA GC | 6924-6946 | | |
| | Probe-TCC AAC AAT TGG TCG TGA AAC AGC TCG | 6873-6899 | | |
| wzy (O118) | ATA TTT GCA CGA TTT ACA GAT GT | 4396-4418 | DQ990684 | This Study |
| | AAA ATA TGA AGC AAA ATA ACA GCC | 4500-4523 | | |
| | Probe-ATA TTA TTG ATA CCA GTA ATA CTT AAA ATC TCT TCC | 4435-4470 | | |
| wzx (O45) | TAC GTC TGG CTG CAG GG | 7445-7461 | AY771223 | This Study |
| | ACT TGC AGC AAA AAA TCC CC | 7490-7509 | | |
| | Probe-TTC GTT GCG TTG TGC ATG GTG GC | 7465-7487 | | |
| wbgN (O55) | TGT AAT TCG ATG CAC CAA TTC AG | 8851-8873 | AF461121 | This Study |
| | CGC TTC GAC GTT CGA TAC ATA A | 8899-8920 | | |
| | Probe-TCC GTG CAT ATA CGC CGC GGA | 8876-8896 | | |
| eaeα | GAT ACG AAT GGC TAT GCC AAA G | 2459-2482 | M58154 | (Nielsen and Andersen 2003) |
| | CAT CGC TAA CAC GGG CAC TA | 2775-2554 | | |
| | Probe-A ACA TCG ACA ACT CCA GGA AAA TCA CTC GT | 2541-2511 | | |
| eaeβ | GGT GAT AAT CAG AGT GCG ACA TAC A | 3167-3191 | U600002 | (Nielsen and Andersen 2003) |
| | GGC ATC AAA ATA CGT AAC TCG AGT AT | 3259-3234 | | |
| | Probe-CCA CAG CAA TTA CAA TAC TAC CCG GTG CA | 3227-3199 | | |

TABLE 1-continued

Primers and probes preloaded in the GeneDisc.

| Target gene sequence | Forward primer, reverse primer and probe sequences (5'-3') | Location within sequence | GenBank accession number | Reference |
|---|---|---|---|---|
| eaeγ | GAC TGT TAG TGC GAC AGT CAG TGA | 2267-2291 | Z11541 | (Nielsen and Andersen 2003) |
| | TTG TTG TCA ATT TTC AGT TCA TCA AA | 2350-2325 | | |
| | Probe-TGA CCT CAG TCG CTT TAA CCT CAG CC | 2319-2294 | | |
| eaeδ | CAT TAT CCG GTG AAG AAG TGA CTT T | 98-123 | Y13112 | (Nielsen and Andersen 2003) |
| | CAT AAC CAC TCT GAT CGG TCG TTA | 181-158 | | |
| | Probe-CTT TAG TTT TAT CCA ATG CCC CAA AAT CCG | 157-128 | | |
| eaeε | ATA CCC AAA TTG TGA AAA CGG ATA | 2528-2551 | AF116899 | (Nielsen and Andersen 2003) |
| | CAC TAA CAA CAG CAT TAC CTG CAA | 2611-2588 | | |
| | Probe-CCA GAT GTC AGT TTT ACC GTA GCC CTA CCA | 2585-2556 | | |
| eaeζ | GAT GTC AAA GCA CCT GAA GTT GAA | 2224-2247 | AF449417 | (Nielsen and Andersen 2003) |
| | CCC TTT GAT TCC AGT TCC TAC AA | 2310-2288 | | |
| | Probe-TCT TCA CCC CAC TTG CTA TTG ATG ACG G | 2249-2276 | | |
| eaeθ | TGT TAA AGC ACC TGA GGT TAC ATT TT | 5776-5802 | AF025311 | (Nielsen and Andersen 2003) |
| | TCA CCA GTA ACG TTC TTA CCA AGA A | 5859-5835 | | |
| | Probe-TCA ACC TTG TTG TCA ATT TTC AGT CCA TCA | 5832-5802 | | |
| nleB-2 | TATYCTCTGGAACCTATTGATGAAAA | | | |
| | CCTTTTTCGTATCGCTCTGGCC | | | |
| | TTGCTTCAAACCACTGAAAAGAATAGGG G | | | |
| EspK | ATTGTAACTGATGTTATTTCGTTTGG | | | |
| | GRCATCAAAAGCGAAATCACACC | | | |
| | CAGATACTCAATATCACAATCTTTGATATATAAACGACC | | | |

TABLE 2

Virulotyping of the eae and nle genes in EHEC strains

| Serotype | Number tested | ehxA | eae | ent/espL2 | nleB | nleE | nleF | NleH1-2 | nleA |
|---|---|---|---|---|---|---|---|---|---|
| Or[157]:H7, O157:[H7]* | 68[a,b,c] | ehxA | gamma | ent/espL2 | nleB | nleE | nleF | nleH1-2 | nleA |
| O157:[H7] | 6[a,b,c] | ehxA | gamma | ent/espL2 | nleB | nleE | — | nleH1-2 | nleA |
| O157:[H7] | 2[a] | ehxA | gamma | ent/espL2 | nleB | nleE | — | nleH1-2 | — |
| O103:H2 | 23[a,b,c] | ehxA | epsilon | ent/espL2 | nleB | nleE | — | nleH1-2 | — |
| O103:H2 | 2[a,c] | — | epsilon | ent/espL2 | nleB | nleE | — | nleH1-2 | — |
| O103:[H2] | 1 | ehxA | — | ent/espL2 | nleB | nleE | — | nleH1-2 | — |
| O111:[H8] | 20[a,c] | ehxA | theta | ent/espL2 | nleB | nleE | nleF | nleH1-2 | nleA |
| O111:[H-] | 2[a] | ehxA | theta | ent/espL2 | nleB | nleE | nleF | nleH1-2 | nleA |
| O111:H8 | 1[a] | — | theta | ent/espL2 | nleB | nleE | nleF | nleH1-2 | nleA |
| O111:H8 | 1[a] | — | theta | ent/espL2 | nleB | nleE | — | nleH1-2 | nleA |
| O26:[H11] | 21[a,b,c] | ehxA | beta | ent/espL2 | nleB | nleE | nleF | nleH1-2 | nleA |
| O26:[H11] | 7[a] | — | beta | ent/espL2 | nleB | nleE | nleF | nleH1-2 | nleA |
| O26:[H11] | 4[a,c] | ehxA | beta | ent/espL2 | nleB | nleE | — | nleH1-2 | nleA |
| O26:[H11] | 1[a] | — | beta | ent/espL2 | nleB | nleE | — | nleH1-2 | nleA |
| O26:H11 | 1[a] | ehxA | beta | ent/espL2 | nleB | nleE | — | — | nleA |

TABLE 2-continued

Virulotyping of the eae and nle genes in EHEC strains

| Serotype | Number tested | ehxA | eae | ent/espL2 | nleB | nleE | nleF | NleH1-2 | nleA |
|---|---|---|---|---|---|---|---|---|---|
| O145:[H28] | 17[a,c] | ehxA | gamma | ent/espL2 | nleB | nleE | — | nleH1-2 | — |
| O145:H28 | 1[a] | ehxA | gamma | ent/espL2 | nleB | nleE | — | nleH1-2 | nleA |
| O5:H- | 12[a,b] | ehxA | beta | ent/espL2 | nleB | nleE | nleF | nleH1-2 | nleA |
| O55:H7 | 2[a,b] | — | gamma | ent/espL2 | nleB | nleE | nleF | nleH1-2 | nleA |
| O45:H2 | 1[a] | ehxA | epsilon | ent/espL2 | nleB | nleE | — | nleH1-2 | — |
| O118:H16 | 19[a,c] | ehxA | beta | ent/espL2 | nleB | nleE | nleF | nleH1-2 | nleA |
| O118:H16 | 2[a] | — | beta | ent/espL2 | nleB | nleE | nleF | nleH1-2 | nleA |
| O121:H19 | 4[a] | ehxA | epsilon | ent/espL2 | nleB | nleE | nleF | nleH1-2 | nleA |
| O123:H11 | 1[a] | ehxA | beta | ent/espL2 | nleB | nleE | nleF | nleH1-2 | nleA |
| O165:H25 | 1[a] | ehxA | epsilon | ent/espL2 | nleB | nleE | nleF | nleH1-2 | nleA |
| O172:[H25] | 1[a] | ehxA | epsilon | ent/espL2 | nleB | nleE | nleF | nleH1-2 | nleA |
| O15:H2 | 1[a] | — | beta | ent/espL2 | nleB | nleE | — | nleH1-2 | — |
| O103:H25 | 1[a] | ehxA | theta | ent/espL2 | nleB | nleE | nleF | nleH1-2 | nleA |

*six of these were SF O157:NM, and 2 were O-rough:[H7] positive for the $rfbE_{O157}$ gene.
[ ]: genotyping of the flic or rfb genes.
[a]Clinical isolates;
[b]Food isolates;
[c]Animal/environment isolates.

TABLE 3

Virulotyping of the eae and nle genes in stx-negative strains

| Serotype | Number tested | ehxA | eae | ent/espL2 | nleB | nleE | nleF | NleH1-2 | nleA |
|---|---|---|---|---|---|---|---|---|---|
| O103:H2 | 1 | ehxA | epsilon | ent/espL2 | nleB | nleE | — | nleH1-2 | — |
| O103:H2 | 1* | — | beta | ent/espL2 | nleB | nleE | — | nleH1-2 | — |
| O111:H11 | 2 | ehxA | beta | ent/espL2 | nleB | nleE | nleF | nleH1-2 | nleA |
| O111:[H2] | 2 | — | beta | ent/espL2 | nleB | nleE | — | nleH1-2 | — |
| O111:NM | 1 | — | beta | ent/espL2 | nleB | nleE | — | nleH1-2 | — |
| O111:H19 | 2 | — | eta | — | — | — | — | — | — |
| O111:[H25] | 1 | — | theta | ent/espL2 | nleB | nleE | nleF | nleH1-2 | nleA |
| O145:[H28] | 2 | ehxA | gamma | — | — | — | — | nleH1-2 | — |
| O145:H34 | 1 | — | theta | — | — | — | — | — | — |
| O145:H4 | 1 | — | iota | — | — | — | — | — | — |
| O145:Hr | 1 | — | iota | — | — | — | — | — | — |
| O26:[H11] | 7 | — | beta | ent/espL2 | nleB | nleE | nleF | nleH1-2 | nleA |
| O26:H11 | 2 | ehxA | beta | ent/espL2 | nleB | nleE | nleF | nleH1-2 | nleA |
| O26:[H11] | 1 | ehxA | beta | ent/espL2 | nleB | nleE | — | nleH1-2 | nleA |
| O26:[H11] | 1 | — | beta | — | — | — | nleF | nleH1-2 | nleA |
| O26:[H11] | 1 | — | — | — | — | — | nleF | nleH1-2 | nleA |
| O157:H7 | 1** | ehxA | gamma | ent/espL2 | nleB | nleE | nleF | nleH1-2 | nleA |
| O157:[H7] | 2 | ehxA | gamma | ent/espL2 | nleB | nleE | — | nleH1-2 | nleA |
| O157:[HNT] | 1 | — | beta | — | — | — | — | nleH1-2 | nleA |
| O157:H16 | 5 | — | epsilon | — | — | — | — | nleH1-2 | nleA |
| O157:H2 | 1 | — | tau | — | — | — | — | nleH1-2 | nleA |
| O157:H26 | 2 | — | beta | — | — | — | — | nleH1-2 | nleA |
| O157:H27 | 1 | ehxA | Non-typable | — | — | nleE | — | — | nleA |
| O157:H39 | 1 | ehxA | kappa | — | — | nleE | — | — | nleA |
| O157:H45 | 2 | — | alpha | — | — | — | nleF | nleH1-2 | nleA |
| O157:H45 | 1 | — | alpha | — | — | — | nleF | nleH1-2 | — |
| O15:H2 | 1 | — | beta | ent/espL2 | nleB | nleE | — | nleH1-2 | — |
| O55:H7 | 4 | — | gamma | ent/espL2 | nleB | nleE | nleF | nleH1-2 | nleA |
| O121:[H-] | 1 | — | epsilon | ent/espL2 | nleB | nleE | nleF | nleH1-2 | nleA |
| O121:H19 | 3 | ehxA | epsilon | ent/espL2 | nleB | nleE | nleF | nleH1-2 | nleA |
| O121:H19 | 1 | ehxA | — | ent/espL2 | nleB | nleE | nleF | nleH1-2 | nleA |
| O55:H6 | 1 | — | iota | — | — | — | nleF | nleH1-2 | — |
| O128:H2 | 1 | — | beta | — | — | — | — | nleH1-2 | — |
| O113:H6 | 1 | — | beta | — | — | — | — | nleH1-2 | — |
| O127:H6 | 1*** | — | alpha | ent/espL2 | nleB | nleE | nleF | nleH1-2 | nleA |
| O156:H8 | 1 | — | gamma | ent/espL2 | nleB | nleE | — | nleH1-2 | — |
| O84:H2 | 1 | ehxA | zeta | ent/espL2 | nleB | — | nleF | nleH1-2 | nleA |
| O86:H40 | 1 | — | theta | ent/espL2 | nleB | nleE | — | — | — |
| O125:H6 | 1 | — | alpha | — | — | — | — | — | — |
| O126:H6 | 1 | — | alpha | — | — | — | — | — | — |
| O51 | 1 | — | alpha | — | — | — | — | — | — |
| O76:H51 | 1 | — | gamma | — | — | — | — | — | — |

*Reference RDEC strain E22.
**Reference strain ATCC43888.
***Reference EPEC strain E2348/69.

TABLE 4

Strains tested negative for the eae and nle genes.

| Serotype | Number tested | E. coli/others | ehxA |
|---|---|---|---|
| O91:H21 | 11 | Atypical EHEC | ehxA |
| O91:H21 | 4 | Atypical EHEC | — |
| O113:H21 | 8 | Atypical EHEC | ehxA |
| O113:H21 | 3 | Atypical EHEC | — |
| O100:NM | 5 | STEC | — |
| O105:H18 | 2 | STEC | ehxA |
| O109:H- | 1 | STEC | ehxA |
| O110 | 2 | STEC | — |
| O111:H10 | 1 | STEC | — |
| O113:H4 | 10 | STEC | ehxA |
| O113:H4 | 2 | STEC | — |
| O115:H18 | 1 | STEC | ehxA |
| O116:H28 | 1 | STEC | ehxA |
| O117 | 2 | STEC | — |
| O118:H12 | 3 | STEC | — |
| O125 | 1 | STEC | ehxA |
| O126:H8 | 1 | STEC | — |
| O128:H2 | 1 | STEC | ehxA |
| O136 | 3 | STEC | — |
| O138 | 1 | STEC | — |
| O139:H1 | 1 | STEC | — |
| O139:ND | 1 | STEC | — |
| O141:[H4] | 1 | STEC | — |
| O141:H2 | 1 | STEC | — |
| O141ac | 1 | STEC | — |
| O145 | 1 | STEC | — |
| O146:H28 | 1 | STEC | ehxA |
| O146:H28 | 4 | STEC | — |
| O146:H8 | 1 | STEC | — |
| O147 | 1 | STEC | — |
| O149:[H19] | 1 | STEC | ehxA |
| O15:H16 | 1 | STEC | — |
| O168:H8 | 1 | STEC | — |
| O171:H2 | 1 | STEC | — |
| O174:H- | 1 | STEC | — |
| O174:H2 | 5 | STEC | ehxA |
| O174:H21 | 9 | STEC | — |
| O174:H8 | 1 | STEC | — |
| O174:H8 | 1 | STEC | ehxA |
| O178:H19 | 2 | STEC | ehxA |
| O2:H27 | 1 | STEC | ehxA |
| O21:NM | 2 | STEC | ehxA |
| O21:H21 | 4 | STEC | ehxA |
| O22:H16 | 2 | STEC | — |
| O22:H16 | 2 | STEC | ehxA |
| O22:H8 | 2 | STEC | — |
| O22:H8 | 2 | STEC | ehxA |
| O22:Hr | 1 | STEC | ehxA |
| O23:H15 | 1 | STEC | ehxA |
| O3 | 2 | STEC | ehxA |
| O30:H12 | 1 | STEC | — |
| O39:H48 | 1 | STEC | ehxA |
| O40:H21 | 1 | STEC | ehxA |
| O41:H7 | 1 | STEC | — |
| O46:H38 | 2 | STEC | ehxA |
| O48 | 2 | STEC | ehxA |
| O5 | 1 | STEC | ehxA |
| O53 | 2 | STEC | — |
| O55:H19 | 1 | STEC | — |
| O6 | 8 | STEC | — |
| O6:H10 | 1 | STEC | ehxA |
| O6:H4 | 1 | STEC | — |
| O60 | 1 | STEC | — |
| O74:H42 | 1 | STEC | ehxA |
| O75:H8 | 1 | STEC | ehxA |
| O76 | 1 | STEC | ehxA |
| O76:H19 | 1 | STEC | ehxA |
| O76:H19 | 1 | STEC | — |
| O77 | 2 | STEC | ehxA |
| O79 | 1 | STEC | ehxA |
| O79:H48 | 1 | STEC | ehxA |
| O8:H8 | 2 | STEC | — |
| O8:H19 | 4 | STEC | — |
| O8:H19 | 1 | STEC | ehxA |
| O88:H25 | 1 | STEC | — |
| O88 | 1 | STEC | ehxA |
| O91 | 1 | STEC | ehxA |
| O91 | 5 | STEC | — |
| O91:H9 | 1 | STEC | ehxA |
| O91:H10 | 3 | STEC | — |
| O96:H19 | 1 | STEC | ehxA |
| Or:H12 | 1 | STEC | — |
| Or | 2 | STEC | — |
| Ox7:H16 | 1 | STEC | — |
| Or:H16 | 1 | STEC | ehxA |
| Or:H4 | 1 | STEC | — |
| O26:H32 | 1 | ETEC | — |
| O1:K1:NM | 1 | FEC | — |
| O11:NM | 1 | FEC | — |
| O121:H10 | 2 | FEC | — |
| O125:H30 | 1 | FEC | — |
| O127 | 1 | FEC | — |
| O15:H1 | 1 | FEC | — |
| O16:K1:NM | 1 | FEC | — |
| O17:H18 | 1 | FEC | — |
| O18:K1:H7 | 1 | FEC | — |
| O2:H1 | 1 | FEC | — |
| O2:H6 | 1 | FEC | — |
| O2:K1:H7 | 1 | FEC | — |
| O2:NM | 1 | FEC | — |
| O21:H21 | 1 | FEC | — |
| O25:K5 | 1 | FEC | — |
| O4:H5 | 4 | FEC | — |
| O45:K1:H1 | 1 | FEC | — |
| O46:K1:H31 | 1 | FEC | — |
| O6:K+:NM | 1 | FEC | — |
| O7:K1:NM | 1 | FEC | — |
| O75:K5:NM | 1 | FEC | — |
| O78:NM | 1 | FEC | — |
| O83:K1:H33 | 1 | FEC | — |
| O86 | 1 | FEC | — |
| Or:NM | 1 | FEC | — |
| O103:H8 | 1 | EC | — |
| O111:H8 | 1 | EC | — |
| O111:H10 | 1 | EC | — |
| O111:H12 | 1 | EC | — |
| O111:H21 | 1 | EC | — |
| O113:NM | 1 | EC | — |
| O121:[H45] | 1 | EC | — |
| O132:H18 | 1 | EC | — |
| O142 | 2 | EC | — |
| O145 | 2 | EC | — |
| O145:H2 | 1 | EC | — |
| O153:H12 | 1 | EC | — |
| O157, O157:[H7 neg] | 12 | EC | — |
| O157:H10 | 1 | EC | — |
| O157:H12 | 1 | EC | — |
| O157:H15 | 1 | EC | — |
| O157:H16 | 1 | EC | — |
| O157:H19 | 1 | EC | — |
| O157:H25 | 1 | EC | — |
| O157:H42 | 1 | EC | — |
| O157:H43 | 1 | EC | — |
| O2:H1 | 1 | EC | — |
| O26:H21 | 1 | EC | — |
| O55:H19 | 1 | EC | — |
| O6:H4 | 1 | EC | — |
| O62:H30 | 2 | EC | — |
| $O_{NT}$:H7 | 1 | EC | — |
| $O_{NT}$ | 1 | EC | — |
| N/A | 7 | Salmonella sp. | — |
| N/A | 1 | Yersinia | — |
| N/A | 3 | Klebsiella | — |
| N/A | 4 | Proteus | — |
| N/A | 1 | Citrobacter | — |
| N/A | 3 | Hafnia | — |
| N/A | 2 | Shigella | — |
| N/A | 1 | C. sakasaki | — |

TABLE 5

Percentage of EHEC Strains with specified nle gene complement and eae subtype for common EHEC serotypes.

| Serotype (N° strains tested) | % of strains tested | eae | ent/esp2 | nleB | nleE | nleF | nleH1-2 | nleA |
|---|---|---|---|---|---|---|---|---|
| O157:H7 (76) | 89% | γ | ent/esp2 | nleB | nleE | nleF | nleH1-2 | nleA |
|  | 8% | γ | ent/esp2 | nleB | nleE |  | nleH1-2 | nleA |
|  | 3% | γ | ent/esp2 | nleB | nleE |  | nleH1-2 |  |
| O103:H2 (25) | 92% | ε | ent/esp2 | nleB | nleE |  | nleH1-2 |  |
|  | 8% | ε | ent/esp2 | nleB | nleE |  | nleH1-2 |  |
| O111:H8/H- (24) | 92% | θ | ent/esp2 | nleB | nleE | nleF | nleH1-2 | nleA |
|  | 4% | θ | ent/esp2 | nleB | nleE | nleF | nleH1-2 | nleA |
|  | 4% | θ | ent/esp2 | nleB | nleE |  | nleH1-2 | nleA |
| O26:H11 (34) | 62% | β | ent/esp2 | nleB | nleE | nleF | nleH1-2 | nleA |
|  | 20% | β | ent/esp2 | nleB | nleE | nleF | nleH1-2 | nleA |
|  | 12% | β | ent/esp2 | nleB | nleE |  | nleH1-2 | nleA |
|  | 3% | β | ent/esp2 | nleB | nleE |  | nleH1-2 |  |
|  | 3% | β | ent/esp2 | nleB | nleE |  |  | nleA |
| O145:H28 (18) | 94% | γ | ent/esp2 | nleB | nleE |  | nleH1-2 |  |
|  | 6% | γ | ent/esp2 | nleB | nleE |  | nleH1-2 | nleA |

TABLE 6 nle gene complement and eae subtype for uncommon EHEC serotypes.

| Serotype | eae | ent/esp2 | nleB | nleE | nleF | nleH1-2 | nleA |
|---|---|---|---|---|---|---|---|
| O5:H- | β | ent/esp2 | nleB | nleE | nleF | nleH1-2 | nleA |
| O55:H7 | γ | ent/esp2 | nleB | nleE |  | nleH1-2 | nleA |
| O45:H2 | ε | ent/esp2 | nleB | nleE |  | nleH1-2 |  |
| O118:H16 | β | ent/esp2 | nleB | nleE | nleF | nleH1-2 | nleA |
| O118:H16 | β | ent/esp2 | nleB | nleE | nleF | nleH1-2 | nleA |
| O121:H19 | ε | ent/esp2 | nleB | nleE | nleF | nleH1-2 | nleA |
| O123:H11 | β | ent/esp2 | nleB | nleE | nleF | nleH1-2 | nleA |
| O165:H25 | ε | ent/esp2 | nleB | nleE | nleF | nleH1-2 | nleA |
| O172:H25 | ε | ent/esp2 | nleB | nleE | nleF | nleH1-2 | nleA |
| O15:H2 | β | ent/esp2 | nleB | nleE |  | nleH1-2 |  |
| O103:H25 | θ | ent/esp2 | nleB | nleE | nleF | nleH1-2 | nleA |

TABLE 7

Presence of EHEC- and EPEC-associated genetic markers in *E. coli* strains and association with nleB alleles

|  |  | stx | eae | espk | nleB | nleB2* |
|---|---|---|---|---|---|---|
| Typical EHEC | O103:H2/H- (n = 14) | + | + | + | + | + |
|  | O145:H28/H- (n = 12) | + | + | + | + | + |
|  | O111:H8/H- (n = 14) | + | + | + | + | + |
|  | O157:H7/H- (n = 50) | + | + | + | + | + |
|  | O26:H11/H- (n = 30) | + | + | + | + | + |
|  | O121:H19/H- (n = 6) | + | + | + | + | + |
| EPEC | O100:H- (n = 1) | − | + | + | + | + |
|  | O111:H11 (n = 2) | − | + | + | + | + |
|  | O117:H25 (n = 1) | − | + | + | + | + |
|  | O119:H8 (n = 2) | − | + | + | + | + |
|  | O119:H25/H- (n = 2) | − | + | + | + | + |
|  | O222?:H7 (n = 1) | − | + | + | + | + |
|  | O76:H41 (n = 1) | − | + | + | + | + |
|  | O76:H7 (n = 4) | − | + | + | + | + |
|  | O80:H- (n = 3) | − | + | + | + | + |
|  | O84:H- (n = 1) | − | + | + | + | + |
|  | Ont:H2 (n = 2) | − | + | + | + | + |
| Typical EPEC | O103:H2 (n = 1) | − | + | + | + | − |
|  | O114:H2 (n = 10) | − | + | + | + | − |
|  | O119:H2 (n = 1) | − | + | + | + | − |
|  | O128:H- (n = 1) | − | + | + | + | − |
|  | Ont:H2 (n = 1) | − | + | + | + | − |
| EPEC | O111:H19 (n = 3) | − | + | + | − | − |
|  | O111:H9 (n = 3) | − | + | + | − | − |
|  | O115:H38 (n = 1) | − | + | + | − | − |
|  | O119:H9 (n = 1) | − | + | + | − | − |
|  | O145:H1 (n = 1) | − | + | + | − | − |
|  | O145:H19 (n = 1) | − | + | + | − | − |
|  | O145:H28 (n = 2) | − | + | + | − | − |
|  | O157:H26 (n = 1) | − | + | + | − | − |
|  | O28:H28 (n = 3) | − | + | + | − | − |
|  | O49:H35/H10 (n = 1) | − | + | + | − | − |
|  | Ont:H26 (n = 1) | − | + | + | − | − |
|  | Ont:NM (n = 1) | − | + | + | − | − |
| EPEC | O100:H25 (n = 1) | − | + | − | + | + |
|  | O109?:H25 (n = 1) | − | + | − | + | + |
|  | O111:H25 (n = 1) | − | + | − | + | + |
|  | O117:H40b (n = 3) | − | + | − | + | + |
|  | O118:H8a (n = 3) | − | + | − | + | + |
|  | O119:H25 (n = 1) | − | + | − | + | + |
|  | O127 (n = 4) | − | + | − | + | + |
|  | O127:H40 (n = 3) | − | + | − | + | + |
|  | O127:H8 (n = 1) | − | + | − | + | + |
|  | O128:H2 (n = 1) | − | + | − | + | + |
|  | O128:H8 (n = 1) | − | + | − | + | + |
|  | O15:H11 (n = 1) | − | + | − | + | + |
|  | O15:H2 (n = 2) | − | + | − | + | + |
|  | O153:H14 (n = 1) | − | + | − | + | + |
|  | O156:H8 (n = 1) | − | + | − | + | + |
|  | O2:H40b (n = 1) | − | + | − | + | + |
|  | O2:H8 (n = 1) | − | + | − | + | + |
|  | O2:H- (n = 2) | − | + | − | + | + |
|  | O21:H25 (n = 1) | − | + | − | + | + |
|  | O26:H11/H- (n = 5) | − | + | − | + | + |
|  | O3:H40b (n = 1) | − | + | − | + | + |
|  | O3:H5 (n = 1) | − | + | − | + | + |
|  | O3:H8a (n = 3) | − | + | − | + | + |
|  | O45:H7 (n = 1) | − | + | − | + | + |
|  | O55 (n = 2) | − | + | − | + | + |

TABLE 7-continued

Presence of EHEC- and EPEC-associated genetic markers in E. coli strains and association with nleB alleles

|  |  | stx | eae | espk | nleB | nleB2* |
|---|---|---|---|---|---|---|
|  | O55:H7 (n = 15) | − | + | − | + | + |
|  | O66:H8a (n = 1) | − | + | − | + | + |
|  | O70:H11 (n = 5) | − | + | − | + | + |
|  | O71:H40b (n = 1) | − | + | − | + | + |
|  | O76:H7 (n = 1) | − | + | − | + | + |
|  | O86:H11 (n = 2) | − | + | − | + | + |
|  | ONT:H21 (n = 4) | − | + | − | + | + |
|  | Orough/H40b (n = 2) | − | + | − | + | + |
|  | Orough:H8a (n = 1) | − | + | − | + | + |
|  | OX177:H11 (n = 2) | − | + | − | + | + |
| Typical EPEC | O111:H2 (n = 17) | − | + | − | + | − |
|  | O111:H25 (n = 1) | − | + | − | + | − |
|  | O119:H2 (n = 2) | − | + | − | + | − |
|  | O126:H27 (n = 1) | − | + | − | + | − |
|  | O127:H6 (n = 1) | − | + | − | + | − |
|  | O128:H2 (n = 1) | − | + | − | + | − |
|  | O55:H6 (n = 5) | − | + | − | + | − |
|  | O119s:H2 (n = 1) | − | + | − | + | − |
|  | O142:H6 (n = 3) | − | + | − | + | − |
|  | Orough:H7 | − | + | − | + | − |
| EPEC | O102:H19 (n = 1) | − | + | − | − | − |
|  | O103:H2 (n = 1) | − | + | − | − | − |
|  | O108:H9 (n = 6) | − | + | − | − | − |
|  | O111:H2 (n = 1) | − | + | − | − | − |
|  | O113:H6 (n = 1) | − | + | − | − | − |
|  | O114:H49 (n = 5) | − | + | − | − | − |
|  | O115:H38 (n = 2) | − | + | − | − | − |
|  | O118:H5 (n = 1) | − | + | − | − | − |
|  | O119:H6 (n = 4) | − | + | − | − | − |
|  | O119:NT (n = 1) | − | + | − | − | − |
|  | O123/O4:H45 (n = 2) | − | + | − | − | − |
|  | O123:H25 (n = 1) | − | + | − | − | − |
|  | O125ac:H6 (n = 6) | − | + | − | − | − |
|  | O126:H27 (n = 1) | − | + | − | − | − |
|  | O127:H19 (n = 1) | − | + | − | − | − |
|  | O127:H21 (n = 1) | − | + | − | − | − |
|  | O128:H2 (n = 10) | − | + | − | − | − |
|  | O142:H34 (n = 1) | − | + | − | − | − |
|  | O145:H34 (n = 5) | − | + | − | − | − |
|  | O150:H8 (n = 1) | − | + | − | − | − |
|  | O157 (n = 2) | − | + | − | − | − |
|  | O157:H16 (n = 4) | − | + | − | − | − |
|  | O157:H45 (n = 1) | − | + | − | − | − |
|  | O168:H-/? (n = 1) | − | + | − | − | − |
|  | O177:H26 (n = 1) | − | + | − | − | − |
|  | O26:H11 (n = 1) | − | + | − | − | − |
|  | O28:H28 | − | + | − | − | − |
|  | O4:H16 (n = 1) | − | + | − | − | − |
|  | O45:H9 (n = 1) | − | + | − | − | − |
|  | O49:H10/H- (n = 2) | − | + | − | − | − |
|  | O5:H- (n = 1) | − | + | − | − | − |
|  | O5:H11 (n = 1) | − | + | − | − | − |
|  | O51:H49 (n = 3) | − | + | − | − | − |
|  | O55 (n = 1) | − | + | − | − | − |
|  | O55:H37 (n = 1) | − | + | − | − | − |
|  | O55:H7 (n = 1) | − | + | − | − | − |
|  | O62:H9 (n = 1) | − | + | − | − | − |
|  | O63:H-H6 (n = 2) | − | + | − | − | − |
|  | O65:H-H25 (n = 1) | − | + | − | − | − |
|  | O69:H2 (n = 1) | − | + | − | − | − |
|  | O69:H16 (n = 2) | − | + | − | − | − |
|  | O70/O86:H2 (n = 1) | − | + | − | − | − |
|  | O86 (n = 2) | − | + | − | − | − |
|  | O86:H34 (n = 2) | − | + | − | − | − |
|  | O86:H8 (n = 4) | − | + | − | − | − |
|  | O86:NT (n = 1) | − | + | − | − | − |
|  | O88:H8a (n = 1) | − | + | − | − | − |
|  | O9/O25:H10 (n = 1) | − | + | − | − | − |
|  | OK8:H10 (n = 1) | − | + | − | − | − |
|  | Ont:H11 (n = 1) | − | + | − | − | − |
|  | Ont:H14 (n = 1) | − | + | − | − | − |
|  | Ont:H2 (n = 3) | − | + | − | − | − |
|  | Ont:H24 (n = 1) | − | + | − | − | − |
|  | Ont:H40b (n = 1) | − | + | − | − | − |
|  | Ont:H6 (n = 1) | − | + | − | − | − |
|  | Ont:H7 (n = 1) | − | + | − | − | − |
|  | Ont:Hrough (n = 1) | − | + | − | − | − |
|  | Ont:H- (n = 1) | − | + | − | − | − |
|  | Orough:H10 (n = 1) | − | + | − | − | − |
|  | Orough:H6 (n = 1) | − | + | − | − | − |
|  | Orough:H9 (n = 1) | − | + | − | − | − |
|  | OX177:H6 (n = 1) | − | + | − | − | − |

*: "−" means PCR negative or high Ct values obtained with the nleB2 primers set.

REFERENCES

Anonymous. 2005. European Commission Annual Report 2005: surveillance of enteric pathogens in Europe and beyond; 1786/2002/EC. International surveillance network for the enteric infections—*Salmonella*, VTEC O157 and *Campylobacter*. European Commission, Brussels, Belgium.

Beutin, L., A. Miko, G. Krause, K. Pries, S. Haby, K. Steege, and N. Albrecht. 2007. Identification of human-pathogenic strains of Shiga toxin-producing *Escherichia coli* from food by a combination of serotyping and molecular typing of Shiga toxin genes. Appl. Environ. Microbiol. 73(15): 4769-4775.

Beutin, L., G. Krause, S. Zimmermann, S. Kaulfuss, and K. Gleier. 2004. Characterization of Shiga toxin-producing *Escherichia coli* strains isolated from human patients in Germany over a 3-year period. J. Clin. Microbiol. 42: 1099-1108.

Beutin, L., H. Steinruck, G. Krause, K. Steege, S. Haby, G. Hultsch, and B. Appel. 2007. Comparative evaluation of the Ridascreen® Verotoxin enzyme immunoassay for detection of Shiga-toxin producing strains of *Escherichia coli* (STEC) from food and other sources. J. Appl. Microbiol. 102: 630-639.

Beutin, L., S. Jahn, and P. Fach. 2009. Evaluation of the 'GeneDisc' real-time PCR system for detection of enterohaemorrhagic *Escherichia coli* (EHEC) O26, O103, O111, O145 and O157 strains according to their virulence markers and their O- and H-antigen-associated genes. J. Appl. Microbiol. 106(4): 1122-1132.

Bielaszewska, M., R. Köck, A. W. Friedrich, C. Von Eiff, L. B. Zimmerhackl, H. Karch, and A. Mellmann. 2007. Shiga toxin—mediated hemolytic uremic syndrome: time to change the diagnostic paradigm? PLoS One. 2(10): e1024.

Brooks, J. T., E. G. Sowers, J. G. Wells, K. D. Greene, P. M. Griffin, R. M. Hoekstra, and N. A. Strockbine. 2005. Non-O157 Shiga toxin-producing *Escherichia coli* infections in the United States, 1983-2002. J. Infect. Dis. 192(8): 1422-1429.

Chang, C. 1991 "Branched DNA Amplification Multimers for the Sensitive, Direct Detection of Human Hepatitis Viruses," Nucleic Acids Symposium Series, no. 24: 197-200.

Compton, J. 1991 "Nucleic Acid Sequence-Based Amplification," Nature 350, no. 6313: 91-92.

Creuzburg, K., and H. Schmidt. 2007. Molecular characterization and distribution of genes encoding members of the type III effector nleA family among pathogenic *Escherichia coli* strains. J. Clin. Microbiol. 45(8): 2498-2507.

EFSA. 2007. Scientific opinion of the panel on biological hazards on a request from EFSA on monitoring of verotoxigenic *Escherichia coli* (VTEC) and identification of human pathogenic types. The EFSA Journal 579: 1-61.

Eklund, M., F, Scheutz, and A. Siitonen. 2001. Clinical isolates of non-O157 Shiga toxin-producing *Escherichia coli*: serotypes, virulence characteristics, and molecular profiles of strains of the same serotype. J. Clin. Microbiol. 39(8): 2829-2834.

Elliott, S. J., L. A. Wainwright, T. K. McDaniel, K. G. Jarvis, Y. K. Deng, L. C. Lai, B. P. McNamara, M. S. Donnenberg, and J. B. Kaper. 1998. The complete sequence of the locus of enterocyte effacement (LEE) from enteropathogenic *Escherichia coli* E2348/69. Mol. Microbiol. 28(1): 1-4.

Ewing, W. H. 1986. Differentiation of Enterobacteriaceae by Biochemical Reactions. In *Edwards and Ewing's Identification of Enterobacteriaceae* ed. Ewing, W. H. pp. 47-72. Elsevier Science Publishing Co.

Fach, P., S. Perelle, F. Dilasser, and J. Grout. 2001. Comparison between a PCRELISA test and the Vero cell assay for detecting Shiga toxin-producing *Escherichia coli* in dairy products and characterization of virulence traits of the isolated strains. J. Appl. Microbiol. 90: 809-818.

Friedrich, A. W., W. Zhang, M. Bielaszewska, A. Mellmann, R. Köck, A. Fruth, H. Tschäpe, and H. Karch. 2007. Prevalence, virulence profiles, and clinical significance of Shiga toxin-negative variants of enterohemorrhagic *Escherichia coli* O157 infection in humans. Clin. Infect. Dis. 45(1): 39-45.

Karmali, M. A., B. T. Steele, M. Petric, and C. Lim. 1983. Sporadic cases of haemolytic-uraemic syndrome associated with faecal cytotoxin and cytotoxin-producing *Escherichia coli* in stools. Lancet. 1(8325): 619-620.

Karmali, M. A., M. Mascarenhas, S. Shen, K. Ziebell, S. Johnson, R. Reid-Smith, J. Isaac-Renton, C. Clark, K. Rahn, and J. B. Kaper. 2003. Association of genomic O island 122 of *Escherichia coli* EDL 933 with verocytotoxin-producing *Escherichia coli* seropathotypes that are linked to epidemic and/or serious disease. J. Clin. Microbiol. 41: 4930-4940.

Kozub-Witkowski, E., G. Krause, G. Frankel, D. Kramer, B. Appel, and L. Beutin. 2008. Serotypes and virutypes of enteropathogenic and enterohaemorrhagic *Escherichia coli* strains from stool samples of children with diarrhoea in Germany. J. Appl. Microbiol. 104: 403-410.

Lawrence, J. G. 2005. Common themes in the genome strategies of pathogens. Curr. Opin. Genet. Dev. 15: 584-588.

Levine, M. M. 1987. *Escherichia coli* That Cause Diarrhea—Enterotoxigenic, Enteropathogenic, Enteroinvasive, Enterohemorrhagic, and Enteroadherent. J. Infect. Dis. 155: 377-389.

Loukiadis, E., Kérourédan, M., Beutin, L., Oswald, E., and Brugère, H., 2006. Characterization of Shiga Toxin Gene (stx)-Positive and Intimin Gene (eae)-Positive *Escherichia coli* Isolates from Wastewater of Slaughterhouses in France. Appl. Envir. Microbiol., May; 72: 3245-3251.

Mackay, I. 2007. Real-time PCR in Microbiology, from diagnosis to characterization. Caister Academic Press, Norfolk, UK.

Maidhof, H., B. Guerra, S. Abbas, H. M. Elsheikha, T. S. Whittam, and L. Beutin. 2002. A multiresistant clone of Shiga toxin-producing *Escherichia coli* O118:[H16] is spread in cattle and humans over different European countries. Appl. Environ. Microbiol. 68(12): 5834-5842.

McLean, C., K. A. Bettelheim, A. Kuzevski, L. Falconer, and S. P. Djordjevic. 2005. Isolation of *Escherichia coli* O5:H—, possessing genes for Shiga toxin 1, intimin-β and enterohaemolysin, from an intestinal biopsy from an adult case of bloody diarrhoea: evidence for two distinct O5:H— pathotypes. J. Med. Microbiol. 54: 605-607.

Nataro, J. P. and J. B. Kaper. 1998. Diarrheagenic *Escherichia coli*. Clinical Microbiol. Rev. 11: 142-201.

Nielsen, E. M. and M. T. Andersen. 2003. Detection and characterization of verocytotoxin producing *Escherichia coli* by automated 5' nuclease PCR assay. J. Clin. Microbiol. 41: 2884-2893.

Notomi, T., Okayama, H., Masubuchi, H., Yonekawa, T., Watanabe, K., Amino, N., and Hase, T. 2000 Loop-Mediated Isothermal Amplification of DNA. Nucleic Acids Research 28, no. 12: E63.

Oswald, E., H. Schmidt, S. Morabito, H. Karch, O. Marches, and A. Caprioli. 2000. Typing of intimin genes in human and animal enterohemorrhagic and enteropathogenic *Escherichia coli*: characterization of a new intimin variant. Infect. Immun. 68: 64-71.

Perelle, S., F. Dilasser, J. Grout, and P. Fach. 2004. Detection by 5'-nuclease PCR of Shiga toxin producing *Escherichia coli* O26, O55, O91, O103, O111, O113, O145 and O157: H7, associated with the world's most frequent clinical cases. Mol. Cell. Probes. 18: 185-192.

Perna, N. T., G. F. Mayhew, G. Pósfai, S. Elliott, M. S. Donnenberg, J. B. Kaper, and F. R. Blattner. 1998. Molecular evolution of a pathogenicity island from enterohemorrhagic *Escherichia coli* O157:H7. Infect Immun. 66(8): 3810-3817.

Riley, L. W., R. S. Remis, S. D. Helgerson, H. B. McGee, J. G. Wells, B. R. Davis, R. J. Hebert, E. S. Olcott, L. M. Johnson, N. T. Hargrett, P. A. Blake, and M. L. Cohen. 1983. Hemorrhagic colitis associated with a rare *Escherichia coli* serotype. N. Engl. J. Med. 308(12): 681-685.

Schimmer, B., K. Nygard, H. M. Eriksen, J. Lassen, B. A. Lindstedt, L. T. Brandal, G. Kapperud, and P. Aavitsland. 2008. Outbreak of haemolytic uraemic syndrome in Norway caused by stx2-positive *Escherichia coli* O103:H25 traced to cured mutton sausages. BMC Infect. Dis. 8:41

Starr, M., V. Bennett-Wood, A. K. Bigham, T. F. de Koning-Ward, A. M. Bordun, D. Lightfoot, K. A. Bettelheim, C. L. Jones, and R. M. Robins-Browne. 1998. Hemolytic-uremic syndrome following urinary tract infection with enterohemorrhagic *Escherichia coli*: case report and review. Clin Infect Dis. 27(2): 310-315.

Tarr, C. L. and T. S. Whittam. 2002. Molecular evolution of the intimin gene in O111 clones of pathogenic *Escherichia coli*. J. Bacteriol. 184: 479-487.

Walker, G., Fraiser, M., Schram, J., Little, M., Nadeau, J., and Douglas P. Malinowski, D. 1992 Strand Displacement Amplification—An Isothermal, In Vitro DNA Amplification Technique, Nucleic Acids Research 20, no. 7: 1691-1696.

Werber, D., L. Beutin, R. Pichner, K. Stark, and A. Fruth. 2008. Shiga Toxin-producing *Escherichia coli* Serogroups in Food and Patients, Germany. Emerg Infect Dis. November; 14(11): 1803-1806.

Yaradou, D. F., S. Hallier-Soulier, S. Moreau, F. Poty, Y. Hillion, M. Reyrolle, J. Andre, G. Festoc, K. Delabre, F. Vandenesch, J. Etienne, and S. Jarraud. 2007. Integrated real-time PCR for detection and monitoring of *Legionella. pneumophila* in water systems. App. Environment. Microbiol. 73: 1452-1456.

Zhang, W. L., B. Kohler, E. Oswald, L. Beutin, H. Karch, S. Morabito, A. Caprioli, S. Suerbaum, and H. Schmidt. 2002. Genetic diversity of intimin genes of attaching and effacing *Escherichia coli* strains. J. Clin. Microbiol. 40: 4486-4492.

The invention claimed is:

1. A process of performing a molecular risk assessment (MRA) upon a sample suspected to contain an enterohemorrhagic *Escherichia coli* (EHEC), consisting of the steps:

(a) contacting said sample or DNA isolated therefrom with:

a pair of primers consisting of SEQ ID NO: 1 and SEQ ID NO: 2 or fragments of at least fifteen nucleotides thereof which target the stx1 and stx2 genes;

one or more pairs of primers chosen from a pair of primers consisting of SEQ ID NO: 7 and SEQ ID NO: 8 or fragments of at least fifteen nucleotides thereof which target the eae gene, and a pair of primers consisting of SEQ ID NO: 82 and SEQ ID NO: 83 or fragments of at least fifteen nucleotides thereof which target the espK gene;

one or more pairs of primers chosen from:

a pair of primers including a first primer consisting of SEQ ID NO: 16, SEQ ID NO: 79 or fragments of at least fifteen nucleotides thereof which target the nleB target gene and a second primer consisting of SEQ ID NO: 17, SEQ ID NO: 80 or fragments of at least fifteen nucleotides thereof which target the nleB target gene;

a pair of primers consisting of SEQ ID NO: 25 and SEQ ID NO: 26 or fragments of at least fifteen nucleotides thereof which target the nleH1-2 gene;

a pair of primers consisting of SEQ ID NO: 19 and SEQ ID NO: 20 or fragments of at least fifteen nucleotides thereof which target the nleE gene; and
a pair of primers consisting of SEQ ID NO: 13 and SEQ ID NO: 14 or fragments of at least fifteen nucleotides thereof which target the ent/espL2 target gene;
and detecting the presence or the absence of an amplification product for each of said target genes, wherein the absence of one or more of the amplification products for said target genes indicates a low risk that the sample is contaminated with an EHEC strain whereas the presence of an amplification product for each of said target genes indicates a high risk that the sample is contaminated with an EHEC strain;
and if the amplification products for each of said genes from step (a) are detected then:
(b) contacting said sample or DNA isolated therefrom with one or more pairs of primers which target the eae gene and determining the eae subtype;
performing a negative PCR control;
and detecting the presence or the absence of an amplification product from said reactions.

2. The process according to claim 1, wherein in step (b) the subtypes of eae detected are selected from the group comprising eae γ, eae β, eae θ, and eae ε.

3. A process of performing a molecular risk assessment (MRA) upon a sample suspected to contain an enterohemorrhagic *Escherichia coli* (EHEC), consisting of the steps:
(a) contacting said sample or DNA isolated therefrom with:
a pair of primers consisting of SEQ ID NO: 1 and SEQ ID NO: 2 or fragments of at least fifteen nucleotides thereof which target the stx1 and stx2 genes;
one or more pairs of primers chosen from a pair of primers consisting of SEQ ID NO: 7 and SEQ ID NO: 8 or fragments of at least fifteen nucleotides thereof which target the eae gene, and a pair of primers consisting of SEQ ID NO: 82 and SEQ ID NO: 83 or fragments of at least fifteen nucleotides thereof which target the espK gene;
and one or more pairs of primers chosen from:
a pair of primers including a first primer consisting of SEQ ID NO: 16, SEQ ID NO: 79 or fragments of at least fifteen nucleotides thereof which target the nleB gene and a second primer consisting of SEQ ID NO: 17, SEQ ID NO: 80 or fragments of at least fifteen nucleotides thereof which target the nleB gene;
a pair of primers consisting of SEQ ID NO: 25 and SEQ ID NO: 26 or fragments of at least fifteen nucleotides thereof which target the nleH1-2 gene;
a pair of primers consisting of SEQ ID NO: 19 and SEQ ID NO: 20 or fragments of at least fifteen nucleotides thereof which target the nleE gene; and
a pair of primers consisting of SEQ ID NO: 13 and SEQ ID NO: 14 or fragments of at least fifteen nucleotides thereof which target the ent/espL2 gene;
and one or more pairs of primers chosen from:
a pair of primers consisting of SEQ ID NO: 31 and SEQ ID NO: 32 or fragments of at least fifteen nucleotides thereof which target the rfbE (O157) gene;
a pair of primers consisting of SEQ ID NO: 34 and SEQ ID NO: 35 or fragments of at least fifteen nucleotides thereof which target the wbdl (O111) gene;
a pair of primers consisting of SEQ ID NO: 37 and SEQ ID NO: 38 or fragments of at least fifteen nucleotides thereof which target the wzx (O26) gene;
a pair of primers consisting of SEQ ID NO: 40 and SEQ ID NO: 41 or fragments of at least fifteen nucleotides thereof which target the ihpl (O145) gene;
a pair of primers consisting of SEQ ID NO: 43 and SEQ ID NO: 44 or fragments of at least fifteen nucleotides thereof which target the wzx (O103) gene;
and detecting the presence or the absence of an amplification product for each of said target genes, wherein the absence of one or more of the amplification products for said target genes indicates a low risk that the sample is contaminated with an EHEC strain whereas the presence of an amplification product for each of said target genes indicates a high risk that the sample is contaminated with an EHEC strain;
and if the amplification products for each of said genes from step (a) are detected then:
(b) contacting said sample or DNA isolated therefrom with one or more pairs of primers derived from the eae target gene and determining the eae subtype;
and performing a negative PCR control;
and detecting the presence or the absence of an amplification product from said reactions.

4. The process according to claim 3, consisting of the steps:
(a) contacting the sample or DNA isolated therefrom with:
a pair of primers consisting of SEQ ID NO: 1 and SEQ ID NO: 2 or fragments of at least fifteen nucleotides thereof which target the stx1 and stx2 genes; and
a pair of primers consisting of SEQ ID NO: 7 and SEQ ID NO: 8 or fragments of at least fifteen nucleotides thereof which target the eae gene; and
a pair of primers consisting of SEQ ID NO:82olKQL and NO: 83 or fragments of at least fifteen nucleotides thereof which target the espK gene; and
a pair of primers including a first primer consisting of SEQ ID NO: 16, SEQ ID NO: 79 or fragments of at least fifteen nucleotides thereof which target the nleB gene and a second primer consisting of SEQ ID NO: 17, SEQ ID NO: 80 or fragments of at least fifteen nucleotides thereof which target the nleB gene, or a pair of primers consisting of SEQ ID NO: 13 and SEQ ID NO: 14 or fragments of at least fifteen nucleotides thereof which target the ent/espL2 gene; and
a pair of primers consisting of SEQ ID NO: 31 and SEQ ID NO: 32 or fragments of at least fifteen nucleotides thereof which target the rfbE (O157) gene;
and detecting the presence or the absence of an amplification product for each of the target genes; and
if the amplification products for each of said genes are detected then:
(b) contacting the sample or DNA isolated therefrom with one or more pairs of primers which target the following genes and/or eae subtype:
eae γ;
eae β;
eae θ;
eae ε;
wbdl (O111);
wzx (O26);
ihpl (O145); and
wzx (O103);

and detecting the presence or the absence of an amplification product for each of the target genes.

5. A process of performing a molecular risk assessment (MRA) upon a sample suspected to contain a enterohemorrhagic *Escherichia coli* (EHEC), consisting of the steps:
contacting said sample or DNA isolated therefrom with:
a pair of primers consisting of SEQ ID NO: 1 and SEQ ID NO: 2 or fragments of at least fifteen nucleotides thereof which target the stx1 and stx2 genes;
one or more pairs of primers chosen from a pair of primers consisting of SEQ ID NO: 7 and SEQ ID NO: 8 or fragments of at least fifteen nucleotides thereof which target the eae gene, and a pair of primers consisting of SEQ ID NO: 82 and SEQ ID NO: 83 or fragments of at least fifteen nucleotides thereof which target the espK gene;
a pair of primers including a first primer consisting of SEQ ID NO: 16, SEQ ID NO: 79 or fragments of at least fifteen nucleotides thereof which target the nleB gene and a second primer consisting of SEQ ID NO: 17, SEQ ID NO: 80 or fragments of at least fifteen nucleotides thereof which target the nleB gene;
a pair of primers consisting of SEQ ID NO: 25 and SEQ ID NO: 26 or fragments of at least fifteen nucleotides thereof which target the nleH1-2 gene;
a pair of primers consisting of SEQ ID NO: 19 and SEQ ID NO: 20 or fragments of at least fifteen nucleotides thereof which target the nleE gene;
a pair of primers consisting of SEQ ID NO: 13 and SEQ ID NO: 14 or fragments of at least fifteen nucleotides thereof which target the ent/espL2 gene; and
detecting the presence or the absence of an amplification product for each of said target genes, wherein the absence of one or more of the amplification products for said target genes indicates a low risk that the sample is contaminated with an EHEC strain whereas the presence of an amplification product for each of said target genes indicates a high risk that the sample is contaminated with an EHEC strain;
performing a negative PCR control;
and detecting the presence or the absence of an amplification product from said reactions.

6. A process of performing a molecular risk assessment (MRA) upon a sample suspected to contain a enterohemorrhagic *Escherichia coli* (EHEC), consisting of the steps:
contacting said sample or DNA isolated therefrom with:
a pair of primers consisting of SEQ ID NO: 1 and SEQ ID NO: 2 or fragments of at least fifteen nucleotides thereof which target the stx1 and stx2 genes;
one or more pairs of primers chosen from a pair of primers consisting of SEQ ID NO: 7 and SEQ ID NO: 8 or fragments of at least fifteen nucleotides thereof which target the eae gene, and a pair of primers consisting SEQ ID NO: 82 and SEQ ID NO: 83 or fragments of at least fifteen nucleotides thereof which target the espK gene;
a pair of primers including a first primer consisting of SEQ ID NO: 16, SEQ ID NO: 79 or fragments of at least fifteen nucleotides thereof which target the nleB gene and a second primer consisting of SEQ ID NO: 17, SEQ ID NO: 80 or fragments of at least fifteen nucleotides thereof which target the nleB gene;
a pair of primers consisting of SEQ ID NO: 25 and SEQ ID NO: 26 or fragments of at least fifteen nucleotides thereof which target the nleH1-2 gene;
a pair of primers consisting of SEQ ID NO: 19 and SEQ ID NO: 20 or fragments of at least fifteen nucleotides thereof which target the nleE gene;
a pair of primers consisting of SEQ ID NO: 13 and SEQ ID NO: 14 or fragments of at least fifteen nucleotides thereof which target the ent/espL2 gene;
one or more pairs of primers chosen from a pair of primers consisting of SEQ ID NO: 10 and SEQ ID NO: 11 or fragments of at least fifteen nucleotides thereof which target the ehxA gene, a pair primers consisting of SEQ ID NO: 22 and SEQ ID NO: 23 or fragments of at least fifteen nucleotides thereof which target the nleF gene; and a pair primers consisting of SEQ ID NO: 28 and SEQ ID NO: 29 or fragments of at least fifteen nucleotides thereof which target the nleA gene;
and detecting the presence or the absence of an amplification product for each of said target genes, wherein the absence of one or more of the amplification products for said target genes indicates a low risk that the sample is contaminated with an EHEC strain whereas the presence of an amplification product for each of said target genes indicates a high risk that the sample is contaminated with an EHEC strain;
performing a negative PCR control;
and detecting the presence or the absence of an amplification product from said reactions.

7. The process according to claim 1, wherein said pair of primers of step (b) for each of said target genes comprise:
at least one primer consisting of SEQ ID NO: 52 or SEQ ID NO: 53, or a fragment of at least fifteen nucleotides thereof which targets the eae γ gene;
at least one primer consisting of SEQ ID NO: 49 or SEQ ID NO: 50, or a fragment of at least fifteen nucleotides thereof which targets the eae β gene;
at least one primer consisting of SEQ ID NO: 64 or SEQ ID NO: 65, or a fragment of at least fifteen nucleotides thereof which targets the eae θ gene; and
at least one primer consisting of SEQ ID NO: 58 or SEQ ID NO: 59, or a fragment of at least fifteen nucleotides thereof which targets the eae ε gene.

8. The process according to claim 1, wherein said amplification products are detected using a degenerate probe consisting of a sequence chosen from:
SEQ ID NO: 3, or a fragment of at least fifteen nucleotides thereof which targets the stx1gene;
SEQ ID NO: 6, or a fragment of at least fifteen nucleotides thereof which targets the stx2 gene;
SEQ ID NO: 9, or a fragment of at least fifteen nucleotides thereof which targets the eae gene;
SEQ ID NO: 84, or a fragment of at least fifteen nucleotides thereof which targets the espK gene;
SEQ ID NO: 18 or SEQ ID NO: 81, or a fragment of at least fifteen nucleotides thereof which targets the nleB gene;
SEQ ID NO: 27, or a fragment of at least fifteen nucleotides thereof which targets the nleH1-2 gene;
SEQ ID NO: 21, or a fragment of at least fifteen nucleotides thereof which targets the nleE gene;
SEQ ID NO: 15, or a fragment of at least fifteen nucleotides thereof which targets the ent/espL2 gene;
SEQ ID NO: 54, or a fragment of at least fifteen nucleotides thereof which targets the eae γ gene;
SEQ ID NO: 51, or a fragment of at least fifteen nucleotides thereof which targets the eae β gene;
SEQ ID NO: 66, or a fragment of at least fifteen nucleotides thereof which targets the eae θ gene;

SEQ ID NO: 60, or a fragment of at least fifteen nucleotides thereof which targets the eae ε gene.

9. The process according to claim 8, wherein said probes are labelled with at least one fluorescent label.

10. The process according to claim 1, wherein said process comprises a multiplex amplification reaction.

11. The process according to claim 1, wherein said process comprises a series of independent amplification reactions.

12. The process according to claim 1, wherein amplification reactions are performed on a macroarray.

13. The process according to claim 1, wherein said amplification reactions are real time PCR reactions.

14. The process according to claim 3, wherein said pair of primers of step (b) comprise:
at least one primer consisting of SEQ ID NO: 52 or SEQ ID NO: 53, or a fragment of at least fifteen nucleotides thereof which targets the eae γ gene;
at least one primer consisting of SEQ ID NO: 49 or SEQ ID NO: 50, or a fragment of at least fifteen nucleotides thereof which targets the eae β gene;
at least one primer consisting of SEQ ID NO: 64 or SEQ ID NO: 65, or a fragment of at least fifteen nucleotides thereof which targets the eae θ gene;
at least one primer consisting of SEQ ID NO: 58 or SEQ ID NO: 59, or a fragment of at least fifteen nucleotides thereof which targets the eae ε gene.

15. The process according to claim 3, wherein said amplification products are detected using a degenerate probe consisting of a sequence chosen from:
SEQ ID NO: 3, or a fragment of at least fifteen nucleotides thereof which targets the stx1 gene;
SEQ ID NO: 6, or a fragment of at least fifteen nucleotides thereof which targets the stx2 gene;
SEQ ID NO: 9, or a fragment of at least fifteen nucleotides thereof which targets the eae gene;
SEQ ID NO: 84, or a fragment of at least fifteen nucleotides thereof which targets the espK gene;
SEQ ID NO: 18 or SEQ ID NO: 81, or a fragment of at least fifteen nucleotides thereof which target the nleB gene;
SEQ ID NO: 27, or a fragment of at least fifteen nucleotides thereof which targets the nleH1-2 gene;
SEQ ID NO: 21, or a fragment of at least fifteen nucleotides thereof which targets the nleE gene;
SEQ ID NO: 15, or a fragment of at least fifteen nucleotides thereof which target the ent/espL2 gene;
SEQ ID NO: 54, or a fragment of at least fifteen nucleotides thereof which targets the eae γ gene;
SEQ ID NO: 51, or a fragment of at least fifteen nucleotides thereof which targets the eae β gene;
SEQ ID NO: 66, or a fragment of at least fifteen nucleotides thereof which targets the eae θ gene;
SEQ ID NO: 60, or a fragment of at least fifteen nucleotides thereof which targets the eae ε gene;
SEQ ID NO: 33, or a fragment of at least fifteen nucleotides thereof which targets the rfbE (O157) gene;
SEQ ID NO: 36, or a fragment of at least fifteen nucleotides thereof which target the wbdl (O111) gene;
SEQ ID NO: 39, or a fragment of at least fifteen nucleotides thereof which targets the wzw (O26) gene;
SEQ ID NO: 42, or a fragment of at least fifteen nucleotides thereof which targets the Ihp1 (O145) gene; and
SEQ ID NO: 45, or a fragment of at least fifteen nucleotides thereof which targets the wzx (O103) gene.

16. The process according to claim 15, wherein said probes are labeled with at least one fluorescent label.

17. The process according to claim 3, wherein amplification reactions are performed on a macroarray.

18. The process according to claim 5, wherein amplification reactions are performed on a macroarray.

19. The process according to claim 5, wherein said amplification products are detected using a degenerate probe consisting of a sequence chosen:
SEQ ID NO: 3, or a fragment of at least fifteen nucleotides thereof which targets the stx1 gene;
SEQ ID NO: 6, or a fragment of at least fifteen nucleotides thereof which targets the stx2 gene;
SEQ ID NO: 9, or a fragment of at least fifteen nucleotides thereof which targets the eae gene;
SEQ ID NO: 84, or a fragment of at least fifteen nucleotides thereof which targets the espK gene;
SEQ ID NO: 18 or SEQ ID NO: 81, or a fragment of at least fifteen nucleotides thereof which targets the nleB gene;
SEQ ID NO: 27, or a fragment of at least fifteen nucleotides thereof which targets the nleH1-2 gene;
SEQ ID NO: 21, or a fragment of at least fifteen nucleotides thereof which targets the nleE gene;
SEQ ID NO: 15, or a fragment of at least fifteen nucleotides thereof which targets the ent/espL2 gene.

20. The process according to claim 19, wherein said probes are labeled with at least one fluorescent label.

21. The process according to claim 6, wherein amplification reactions are performed on a macroarray.

22. The process according to claim 6, wherein said amplification products are detected using a degenerate probe consisting of a sequence chosen from:
SEQ ID NO: 3, or a fragment of at least fifteen nucleotides thereof which targets the stx1 gene;
SEQ ID NO: 6, or a fragment of at least fifteen nucleotides thereof which targets the stx2 gene;
SEQ ID NO: 9, or a fragment of at least fifteen nucleotides thereof which targets the eae gene;
SEQ ID NO: 84, or a fragment of at least fifteen nucleotides thereof which targets the espK gene;
SEQ ID NO: 12, or a fragment of at least fifteen nucleotides thereof which targets the ehxA gene;
SEQ ID NO: 24, or a fragment of at least fifteen nucleotides thereof which targets the nleF gene;
SEQ ID NO: 18 or SEQ ID NO: 81, or a fragment of at least fifteen nucleotides thereof which targets the nleB gene;
SEQ ID NO: 27, or a fragment of at least fifteen nucleotides thereof which targets the nleH1-2 gene;
SEQ ID NO: 21, or a fragment of at least fifteen nucleotides thereof which targets the nleE gene;
SEQ ID NO: 30, or a fragment of at least fifteen nucleotides thereof which targets the nleA gene;
SEQ ID NO: 15, or a fragment of at least fifteen nucleotides thereof which targets the ent/espL2 gene.

23. The process according to claim 22, wherein said probes are labeled with at least one fluorescent label.

* * * * *

SEQUENCE LISTING

<160> NUMBER OF SEQ ID NOS: 84

<210> SEQ ID NO 1
<211> LENGTH: 29
<212> TYPE: DNA
<213> ORGANISM: Artificial
<220> FEATURE:
<223> OTHER INFORMATION: stx1 for primer

<400> SEQUENCE: 1
tttgtyactg tsacagcwga agcyttacg                               29

<210> SEQ ID NO 2
<211> LENGTH: 26
<212> TYPE: DNA
<213> ORGANISM: Artificial
<220> FEATURE:
<223> OTHER INFORMATION: stx1 rev primer

<400> SEQUENCE: 2
ccccagttca rwgtragrtc macrtc                                  26

<210> SEQ ID NO 3
<211> LENGTH: 31
<212> TYPE: DNA
<213> ORGANISM: Artificial
<220> FEATURE:
<223> OTHER INFORMATION: stx1 probe

<400> SEQUENCE: 3
ctggatgatc tcagtgggcg ttcttatgta a                            31

<210> SEQ ID NO 4
<211> LENGTH: 29
<212> TYPE: DNA
<213> ORGANISM: Artificial
<220> FEATURE:
<223> OTHER INFORMATION: stx2 for primer

<400> SEQUENCE: 4
tttgtyactg tsacagcwga agcyttacg                               29

<210> SEQ ID NO 5
<211> LENGTH: 26
<212> TYPE: DNA
<213> ORGANISM: Artificial
<220> FEATURE:
<223> OTHER INFORMATION: stx2 rev primer

<400> SEQUENCE: 5
ccccagttca rwgtragrtc macrtc                                  26

<210> SEQ ID NO 6
<211> LENGTH: 27
<212> TYPE: DNA
<213> ORGANISM: Artificial
<220> FEATURE:
<223> OTHER INFORMATION: stx2 probe

<400> SEQUENCE: 6
tcgtcaggca ctgtctgaaa ctgctcc                                 27

<210> SEQ ID NO 7
<211> LENGTH: 26
<212> TYPE: DNA
<213> ORGANISM: Artificial

```
<220> FEATURE:
<223> OTHER INFORMATION: eae for primer

<400> SEQUENCE: 7
cattgatcag gatttttctg gtgata                                          26

<210> SEQ ID NO 8
<211> LENGTH: 21
<212> TYPE: DNA
<213> ORGANISM: Artificial
<220> FEATURE:
<223> OTHER INFORMATION: eae rev primer

<400> SEQUENCE: 8
ctcatgcgga aatagccgtt a                                               21

<210> SEQ ID NO 9
<211> LENGTH: 29
<212> TYPE: DNA
<213> ORGANISM: Artificial
<220> FEATURE:
<223> OTHER INFORMATION: eae probe

<400> SEQUENCE: 9
atagtctcgc cagtattcgc caccaatac                                       29

<210> SEQ ID NO 10
<211> LENGTH: 21
<212> TYPE: DNA
<213> ORGANISM: Artificial
<220> FEATURE:
<223> OTHER INFORMATION: ehxA for primer

<400> SEQUENCE: 10
gtgtcagtag ggaagcgaac a                                               21

<210> SEQ ID NO 11
<211> LENGTH: 19
<212> TYPE: DNA
<213> ORGANISM: Artificial
<220> FEATURE:
<223> OTHER INFORMATION: ehxA rev primer

<400> SEQUENCE: 11 atcatgttttt ccgccaatg                                                 19

<210> SEQ ID NO 12
<211> LENGTH: 26
<212> TYPE: DNA
<213> ORGANISM: Artificial
<220> FEATURE:
<223> OTHER INFORMATION: ehxA probe

<400> SEQUENCE: 12
cgtgattttg aattcagaac cggtgg                                          26

<210> SEQ ID NO 13
<211> LENGTH: 24
<212> TYPE: DNA
<213> ORGANISM: Artificial
<220> FEATURE:
<223> OTHER INFORMATION: ent/espL2 for primer

<400> SEQUENCE: 13
tcctggatta ttttctgcat ttca                                            24
```

<210> SEQ ID NO 14
<211> LENGTH: 22
<212> TYPE: DNA
<213> ORGANISM: Artificial
<220> FEATURE:
<223> OTHER INFORMATION: ent/espL2 rev primer

<400> SEQUENCE: 14
actattgcca agtacgccac aa                                          22

<210> SEQ ID NO 15
<211> LENGTH: 29
<212> TYPE: DNA
<213> ORGANISM: Artificial
<220> FEATURE:
<223> OTHER INFORMATION: ent/espL2 probe

<400> SEQUENCE: 15
aatggtcatg cagacgcaat aaaggcata                                   29

<210> SEQ ID NO 16
<211> LENGTH: 23
<212> TYPE: DNA
<213> ORGANISM: Artificial
<220> FEATURE:
<223> OTHER INFORMATION: nleB for primer

<400> SEQUENCE: 16
catgttgaag gctggaastt tgt                                         23

<210> SEQ ID NO 17
<211> LENGTH: 20
<212> TYPE: DNA
<213> ORGANISM: Artificial
<220> FEATURE:
<223> OTHER INFORMATION: nleB rev primer

<400> SEQUENCE: 17
ccgctacagg gcgatatgtt                                             20

<210> SEQ ID NO 18
<211> LENGTH: 26
<212> TYPE: DNA
<213> ORGANISM: Artificial
<220> FEATURE:
<223> OTHER INFORMATION: nleB probe

<400> SEQUENCE: 18
acagagacgg gaaaaactgg atgcca                                      26

<210> SEQ ID NO 19
<211> LENGTH: 23
<212> TYPE: DNA
<213> ORGANISM: Artificial
<220> FEATURE:
<223> OTHER INFORMATION: nleE for primer

<400> SEQUENCE: 19
agaagcgttt gaacctattt cca                                         23

<210> SEQ ID NO 20
<211> LENGTH: 19
<212> TYPE: DNA
<213> ORGANISM: Artificial
<220> FEATURE:
<223> OTHER INFORMATION: nle rev primer

<400> SEQUENCE: 20
ttgggcgttt tccggatat                                                    19

<210> SEQ ID NO 21
<211> LENGTH: 25
<212> TYPE: DNA
<213> ORGANISM: Artificial
<220> FEATURE:
<223> OTHER INFORMATION: nleE probe

<400> SEQUENCE: 21
agccagtaca ccggaaggaa gctgg                                             25

<210> SEQ ID NO 22
<211> LENGTH: 26
<212> TYPE: DNA
<213> ORGANISM: Artificial
<220> FEATURE:
<223> OTHER INFORMATION: nleF for primer

<400> SEQUENCE: 22
tgaggtgaga aatgaaaata ctgatg                                            26

<210> SEQ ID NO 23
<211> LENGTH: 25
<212> TYPE: DNA
<213> ORGANISM: Artificial
<220> FEATURE:
<223> OTHER INFORMATION: nleF rev primer

<400> SEQUENCE: 23
ctatccctgt cctctatcgt cattc                                             25

<210> SEQ ID NO 24
<211> LENGTH: 19
<212> TYPE: DNA
<213> ORGANISM: Artificial
<220> FEATURE:
<223> OTHER INFORMATION: nleF probe

<400> SEQUENCE: 24
tgtcggagcg ctgagggcg                                                    19

<210> SEQ ID NO 25
<211> LENGTH: 23
<212> TYPE: DNA
<213> ORGANISM: Artificial
<220> FEATURE:
<223> OTHER INFORMATION: nleH1-2 for primer

<400> SEQUENCE: 25
acaagagaaa gtcatagtgg ttg                                               23

<210> SEQ ID NO 26
<211> LENGTH: 23
<212> TYPE: DNA
<213> ORGANISM: Artificial
<220> FEATURE:
<223> OTHER INFORMATION: nleH1-2 rev primer

<400> SEQUENCE: 26
aatctcyccc ttaggccatc cca                                               23

<210> SEQ ID NO 27

<210> SEQ ID NO 27
<211> LENGTH: 21
<212> TYPE: DNA
<213> ORGANISM: Artificial
<220> FEATURE:
<223> OTHER INFORMATION: nleH1-2 rev probe

<400> SEQUENCE: 27
tttactaatc tgttgcacag g                                    21

<210> SEQ ID NO 28
<211> LENGTH: 25
<212> TYPE: DNA
<213> ORGANISM: Artificial
<220> FEATURE:
<223> OTHER INFORMATION: nleA for primer

<400> SEQUENCE: 28
agataacyct aatactaaat atgcc                                25

<210> SEQ ID NO 29
<211> LENGTH: 25
<212> TYPE: DNA
<213> ORGANISM: Artificial
<220> FEATURE:
<223> OTHER INFORMATION: nleA rev primer

<400> SEQUENCE: 29
gcccaaccat tgcrccgata tgagg                                25

<210> SEQ ID NO 30
<211> LENGTH: 27
<212> TYPE: DNA
<213> ORGANISM: Artificial
<220> FEATURE:
<223> OTHER INFORMATION: nleA probe

<400> SEQUENCE: 30
ttcttaccaa tgctgccgca aatgcgc                              27

<210> SEQ ID NO 31
<211> LENGTH: 25
<212> TYPE: DNA
<213> ORGANISM: Artificial
<220> FEATURE:
<223> OTHER INFORMATION: rfbE (O157) f

<400> SEQUENCE: 31
tttcacacrr arrggatggt ctcaa                                25

<210> SEQ ID NO 32
<211> LENGTH: 24
<212> TYPE: DNA
<213> ORGANISM: Artificial
<220> FEATURE:
<223> OTHER INFORMATION: rfbE (O157) r

<400> SEQUENCE: 32
cgatgagttt atctgcaagg tgat                                 24

<210> SEQ ID NO 33
<211> LENGTH: 30
<212> TYPE: DNA
<213> ORGANISM: Artificial
<220> FEATURE:
<223> OTHER INFORMATION: rfbE (O157) probe

<400> SEQUENCE: 33

-continued

```
aggaccgcag aggaaagaga ggaattaagg                                30

<210> SEQ ID NO 34
<211> LENGTH: 26
<212> TYPE: DNA
<213> ORGANISM: Artificial
<220> FEATURE:
<223> OTHER INFORMATION: wbdl (O111) f

<400> SEQUENCE: 34
cgaggcaaca cattatatag tgcttt                                    26

<210> SEQ ID NO 35
<211> LENGTH: 31
<212> TYPE: DNA
<213> ORGANISM: Artificial
<220> FEATURE:
<223> OTHER INFORMATION: wbdl (O111) r

<400> SEQUENCE: 35
tttttgaata gttatgaaca tcttgtttag c                              31

<210> SEQ ID NO 36
<211> LENGTH: 30
<212> TYPE: DNA
<213> ORGANISM: Artificial
<220> FEATURE:
<223> OTHER INFORMATION: wbdl (O111) probe

<400> SEQUENCE: 36
ttgaatctcc cagatgatca acatcgtgaa                                30

<210> SEQ ID NO 37
<211> LENGTH: 19
<212> TYPE: DNA
<213> ORGANISM: Artificial
<220> FEATURE:
<223> OTHER INFORMATION: wzw (O26) f

<400> SEQUENCE: 37
cgcgacggca gcgaaaatt                                            19

<210> SEQ ID NO 38
<211> LENGTH: 26
<212> TYPE: DNA
<213> ORGANISM: Artificial
<220> FEATURE:
<223> OTHER INFORMATION: wzw (O26) r

<400> SEQUENCE: 38
agcaggcttt tatattctcc aacttt                                    26

<210> SEQ ID NO 39
<211> LENGTH: 33
<212> TYPE: DNA
<213> ORGANISM: Artificial
<220> FEATURE:
<223> OTHER INFORMATION: wzw (O26) probe

<400> SEQUENCE: 39
ccccgttaaa tcaatactat ttcacgaggt tga                            33

<210> SEQ ID NO 40
<211> LENGTH: 26
<212> TYPE: DNA
```

```
<213> ORGANISM: Artificial
<220> FEATURE:
<223> OTHER INFORMATION: Ihp1 (O145) f

<400> SEQUENCE: 40
cgataatatt taccccacca gtacag                                          26

<210> SEQ ID NO 41
<211> LENGTH: 15
<212> TYPE: DNA
<213> ORGANISM: Artificial
<220> FEATURE:
<223> OTHER INFORMATION: Ihp1 (O145) r

<400> SEQUENCE: 41
gccgccgcaa tgctt                                                     15

<210> SEQ ID NO 42
<211> LENGTH: 27
<212> TYPE: DNA
<213> ORGANISM: Artificial
<220> FEATURE:
<223> OTHER INFORMATION: Ihp1 (O145) probe

<400> SEQUENCE: 42
ccgccattca gaatgcacac aatatcg                                        27

<210> SEQ ID NO 43
<211> LENGTH: 24
<212> TYPE: DNA
<213> ORGANISM: Artificial
<220> FEATURE:
<223> OTHER INFORMATION: wzx (O103) f

<400> SEQUENCE: 43
caaggtgatt acgaaaatgc atgt                                           24

<210> SEQ ID NO 44
<211> LENGTH: 23
<212> TYPE: DNA
<213> ORGANISM: Artificial
<220> FEATURE:
<223> OTHER INFORMATION: wzx (O103) r

<400> SEQUENCE: 44
gaaaaaagca ccccgtact tat                                             23

<210> SEQ ID NO 45
<211> LENGTH: 18
<212> TYPE: DNA
<213> ORGANISM: Artificial
<220> FEATURE:
<223> OTHER INFORMATION: wzx (O103) probe

<400> SEQUENCE: 45
catagcctgt tgttttat                                                  18

<210> SEQ ID NO 46
<211> LENGTH: 22
<212> TYPE: DNA
<213> ORGANISM: Artificial
<220> FEATURE:
<223> OTHER INFORMATION: eae  alpha f

<400> SEQUENCE: 46
gatacgaatg gctatgccaa ag                                             22
```

-continued

<210> SEQ ID NO 47
<211> LENGTH: 20
<212> TYPE: DNA
<213> ORGANISM: Artificial
<220> FEATURE:
<223> OTHER INFORMATION: eae alpha r

<400> SEQUENCE: 47
catcgctaac acgggcacta                                              20

<210> SEQ ID NO 48
<211> LENGTH: 30
<212> TYPE: DNA
<213> ORGANISM: Artificial
<220> FEATURE:
<223> OTHER INFORMATION: eae alpha probe

<400> SEQUENCE: 48
aacatcgaca actccaggaa aatcactcgt                                   30

<210> SEQ ID NO 49
<211> LENGTH: 25
<212> TYPE: DNA
<213> ORGANISM: Artificial
<220> FEATURE:
<223> OTHER INFORMATION: eae beta f

<400> SEQUENCE: 49
ggtgataatc agagtgcgac ataca                                        25

<210> SEQ ID NO 50
<211> LENGTH: 26
<212> TYPE: DNA
<213> ORGANISM: Artificial
<220> FEATURE:
<223> OTHER INFORMATION: eae beta r

<400> SEQUENCE: 50
ggcatcaaaa tacgtaactc gagtat                                       26

<210> SEQ ID NO 51
<211> LENGTH: 29
<212> TYPE: DNA
<213> ORGANISM: Artificial
<220> FEATURE:
<223> OTHER INFORMATION: eae beta probe

<400> SEQUENCE: 51
ccacagcaat tacaatacta cccggtgca                                    29

<210> SEQ ID NO 52
<211> LENGTH: 24
<212> TYPE: DNA
<213> ORGANISM: Artificial
<220> FEATURE:
<223> OTHER INFORMATION: eae gamma f

<400> SEQUENCE: 52
gactgttagt gcgacagtca gtga                                         24

<210> SEQ ID NO 53
<211> LENGTH: 26
<212> TYPE: DNA
<213> ORGANISM: Artificial
<220> FEATURE:

<223> OTHER INFORMATION: eae gamma r

<400> SEQUENCE: 53
ttgttgtcaa ttttcagttc atcaaa                                    26

<210> SEQ ID NO 54
<211> LENGTH: 26
<212> TYPE: DNA
<213> ORGANISM: Artificial
<220> FEATURE:
<223> OTHER INFORMATION: eae gamma probe

<400> SEQUENCE: 54
tgacctcagt cgctttaacc tcagcc                                    26

<210> SEQ ID NO 55
<211> LENGTH: 25
<212> TYPE: DNA
<213> ORGANISM: Artificial
<220> FEATURE:
<223> OTHER INFORMATION: eae delta f

<400> SEQUENCE: 55
cattatccgg tgaagaagtg acttt                                     25

<210> SEQ ID NO 56
<211> LENGTH: 24
<212> TYPE: DNA
<213> ORGANISM: Artificial
<220> FEATURE:
<223> OTHER INFORMATION: eae delta r

<400> SEQUENCE: 56
cataaccact ctgatcggtc gtta                                      24

<210> SEQ ID NO 57
<211> LENGTH: 30
<212> TYPE: DNA
<213> ORGANISM: Artificial
<220> FEATURE:
<223> OTHER INFORMATION: eae delta probe

<400> SEQUENCE: 57
ctttagtttt atccaatgcc ccaaaatccg                                30

<210> SEQ ID NO 58
<211> LENGTH: 24
<212> TYPE: DNA
<213> ORGANISM: Artificial
<220> FEATURE:
<223> OTHER INFORMATION: eae epsilon f

<400> SEQUENCE: 58
atacccaaat tgtgaaaacg gata                                      24

<210> SEQ ID NO 59
<211> LENGTH: 24
<212> TYPE: DNA
<213> ORGANISM: Artificial
<220> FEATURE:
<223> OTHER INFORMATION: eae epsilon r

<400> SEQUENCE: 59
cactaacaac agcattacct gcaa                                      24

<210> SEQ ID NO 60
<211> LENGTH: 30
<212> TYPE: DNA
<213> ORGANISM: Artificial
<220> FEATURE:
<223> OTHER INFORMATION: eae epsilon probe

<400> SEQUENCE: 60
ccagatgtca gttttaccgt agccctacca                                    30

<210> SEQ ID NO 61
<211> LENGTH: 24
<212> TYPE: DNA
<213> ORGANISM: Artificial
<220> FEATURE:
<223> OTHER INFORMATION: eae zetha f

<400> SEQUENCE: 61
gatgtcaaag cacctgaagt tgaa                                          24

<210> SEQ ID NO 62
<211> LENGTH: 23
<212> TYPE: DNA
<213> ORGANISM: Artificial
<220> FEATURE:
<223> OTHER INFORMATION: eae zetha r

<400> SEQUENCE: 62
ccctttgatt ccagttccta caa                                           23

<210> SEQ ID NO 63
<211> LENGTH: 28
<212> TYPE: DNA
<213> ORGANISM: Artificial
<220> FEATURE:
<223> OTHER INFORMATION: eae zetha probe

<400> SEQUENCE: 63
tcttcacccc acttgctatt gatgacgg                                      28

<210> SEQ ID NO 64
<211> LENGTH: 26
<212> TYPE: DNA
<213> ORGANISM: Artificial
<220> FEATURE:
<223> OTHER INFORMATION: eae theta f

<400> SEQUENCE: 64
tgttaaagca cctgaggtta catttt                                        26

<210> SEQ ID NO 65
<211> LENGTH: 25
<212> TYPE: DNA
<213> ORGANISM: Artificial
<220> FEATURE:
<223> OTHER INFORMATION: eae theta r

<400> SEQUENCE: 65
tcaccagtaa cgttcttacc aagaa                                         25

<210> SEQ ID NO 66
<211> LENGTH: 30
<212> TYPE: DNA
<213> ORGANISM: Artificial
<220> FEATURE:
<223> OTHER INFORMATION: eae theta probe

<400> SEQUENCE: 66
tcaaccttgt tgtcaattt cagtccatca                                    30

<210> SEQ ID NO 67
<211> LENGTH: 20
<212> TYPE: DNA
<213> ORGANISM: Artificial
<220> FEATURE:
<223> OTHER INFORMATION: wzx (O121) f

<400> SEQUENCE: 67
tggtctctta gacttagggc                                              20

<210> SEQ ID NO 68
<211> LENGTH: 23
<212> TYPE: DNA
<213> ORGANISM: Artificial
<220> FEATURE:
<223> OTHER INFORMATION: wzx (O121)

<400> SEQUENCE: 68
ttagcaattt tctgtagtcc agc                                          23

<210> SEQ ID NO 69
<211> LENGTH: 27
<212> TYPE: DNA
<213> ORGANISM: Artificial
<220> FEATURE:
<223> OTHER INFORMATION: wzx (O121) probe

<400> SEQUENCE: 69
tccaacaatt ggtcgtgaaa cagctcg                                      27

<210> SEQ ID NO 70
<211> LENGTH: 23
<212> TYPE: DNA
<213> ORGANISM: Artificial
<220> FEATURE:
<223> OTHER INFORMATION: wzy (O118) f

<400> SEQUENCE: 70
atatttgcac gatttacaga tgt                                          23

<210> SEQ ID NO 71
<211> LENGTH: 24
<212> TYPE: DNA
<213> ORGANISM: Artificial
<220> FEATURE:
<223> OTHER INFORMATION: wzy (O118) r

<400> SEQUENCE: 71
aaaatatgaa gcaaaataac agcc                                         24

<210> SEQ ID NO 72
<211> LENGTH: 36
<212> TYPE: DNA
<213> ORGANISM: Artificial
<220> FEATURE:
<223> OTHER INFORMATION: wzy (O118) probe

<400> SEQUENCE: 72
atattattga taccagtaat acttaaaatc tcttcc                            36

<210> SEQ ID NO 73
<211> LENGTH: 17

```
<212> TYPE: DNA
<213> ORGANISM: Artificial
<220> FEATURE:
<223> OTHER INFORMATION: wzx (O45) f

<400> SEQUENCE: 73
tacgtctggc tgcaggg                                                    17

<210> SEQ ID NO 74
<211> LENGTH: 20
<212> TYPE: DNA
<213> ORGANISM: Artificial
<220> FEATURE:
<223> OTHER INFORMATION: wzx (O45) r

<400> SEQUENCE: 74
acttgcagca aaaatcccc                                                  20

<210> SEQ ID NO 75
<211> LENGTH: 23
<212> TYPE: DNA
<213> ORGANISM: Artificial
<220> FEATURE:
<223> OTHER INFORMATION: wzx (O45) probe

<400> SEQUENCE: 75
ttcgttgcgt tgtgcatggt ggc                                             23

<210> SEQ ID NO 76
<211> LENGTH: 23
<212> TYPE: DNA
<213> ORGANISM: Artificial
<220> FEATURE:
<223> OTHER INFORMATION: wbgN (O55) f

<400> SEQUENCE: 76
tgtaattcga tgcaccaatt cag                                             23

<210> SEQ ID NO 77
<211> LENGTH: 22
<212> TYPE: DNA
<213> ORGANISM: Artificial
<220> FEATURE:
<223> OTHER INFORMATION: wbgN (O55) r

<400> SEQUENCE: 77
cgcttcgacg ttcgatacat aa                                              22

<210> SEQ ID NO 78
<211> LENGTH: 21
<212> TYPE: DNA
<213> ORGANISM: Artificial
<220> FEATURE:
<223> OTHER INFORMATION: wbgN (O55) probe

<400> SEQUENCE: 78
tccgtgcata tacgccgcgg a                                               21

<210> SEQ ID NO 79
<211> LENGTH: 26
<212> TYPE: DNA
<213> ORGANISM: Artificial
<220> FEATURE:
<223> OTHER INFORMATION: nleB-2 f

<400> SEQUENCE: 79
```

```
<210> SEQ ID NO 80
<211> LENGTH: 22
<212> TYPE: DNA
<213> ORGANISM: Artificial
<220> FEATURE:
<223> OTHER INFORMATION: nleB-2 r

<400> SEQUENCE: 80 ccttttttcgt atcgctctgg cc                                             22

<210> SEQ ID NO 81
<211> LENGTH: 30
<212> TYPE: DNA
<213> ORGANISM: Artificial
<220> FEATURE:
<223> OTHER INFORMATION: nleB-2 taq

<400> SEQUENCE: 81
ttgcttcaaa ccactgaaaa agaatagggg                                      30

<210> SEQ ID NO 82
<211> LENGTH: 26
<212> TYPE: DNA
<213> ORGANISM: Artificial
<220> FEATURE:
<223> OTHER INFORMATION: espK f

<400> SEQUENCE: 82
attgtaactg atgttatttc gtttgg                                          26

<210> SEQ ID NO 83
<211> LENGTH: 23
<212> TYPE: DNA
<213> ORGANISM: Artificial
<220> FEATURE:
<223> OTHER INFORMATION: espK r

<400> SEQUENCE: 83
grcatcaaaa gcgaaatcac acc                                             23

<210> SEQ ID NO 84
<211> LENGTH: 39
<212> TYPE: DNA
<213> ORGANISM: Artificial
<220> FEATURE:
<223> OTHER INFORMATION: espK probe

<400> SEQUENCE: 84
cagatactca atatcacaat ctttgatata taaacgacc                            39
```